United States Patent
Alyami

(10) Patent No.: US 9,943,381 B2
(45) Date of Patent: Apr. 17, 2018

(54) METHOD AND DEVICE FOR BIOENGINEERING BONE TISSUE AND MODULATING THE HOMEOSTASIS OF OSTEOGENESIS

(71) Applicant: Bandar Alyami, New York, NY (US)

(72) Inventor: Bandar Alyami, New York, NY (US)

(*) Notice: Subject to any disclaimer, the term of this patent is extended or adjusted under 35 U.S.C. 154(b) by 160 days.

(21) Appl. No.: 14/717,792

(22) Filed: May 20, 2015

(65) Prior Publication Data

US 2016/0339060 A1    Nov. 24, 2016

(51) Int. Cl.
| | | |
|---|---|---|
| *A61C 7/00* | (2006.01) | |
| *A61C 7/10* | (2006.01) | |
| *A61C 7/06* | (2006.01) | |
| *A61B 17/66* | (2006.01) | |
| *A61B 17/34* | (2006.01) | |
| *A61K 9/06* | (2006.01) | |
| *A61K 35/32* | (2015.01) | |
| *A61K 45/06* | (2006.01) | |
| *A61K 47/36* | (2006.01) | |
| *A61B 34/35* | (2016.01) | |
| *A61B 17/80* | (2006.01) | |
| *A61C 7/14* | (2006.01) | |
| *A61C 8/00* | (2006.01) | |
| *A61B 17/00* | (2006.01) | |

(52) U.S. Cl.
CPC .......... *A61C 7/002* (2013.01); *A61B 17/3472* (2013.01); *A61B 17/663* (2013.01); *A61B 17/8071* (2013.01); *A61B 34/35* (2016.02); *A61C 7/06* (2013.01); *A61C 7/10* (2013.01); *A61C 7/145* (2013.01); *A61C 8/0096* (2013.01); *A61K 9/06* (2013.01); *A61K 35/32* (2013.01); *A61K 45/06* (2013.01); *A61K 47/36* (2013.01); *A61B 2017/00221* (2013.01)

(58) Field of Classification Search
None
See application file for complete search history.

(56) References Cited

U.S. PATENT DOCUMENTS

| | | | |
|---|---|---|---|
| 5,112,354 A | 5/1992 | Sires | |
| 5,330,357 A | 7/1994 | Keller | |
| 7,241,732 B2 * | 7/2007 | Puzas | A61L 27/227 514/15.4 |
| 8,313,328 B2 | 11/2012 | Szymaitis | |
| 2002/0004225 A1 * | 1/2002 | Hart | A61K 9/2027 435/69.1 |
| 2007/0082395 A1 * | 4/2007 | Baroli | C12N 5/0643 435/325 |
| 2008/0187518 A1 * | 8/2008 | Ogle | C12N 5/0654 424/93.7 |
| 2008/0318859 A1 * | 12/2008 | Hollander | A61K 38/29 514/16.6 |
| 2010/0183561 A1 | 7/2010 | Sakthivel et al. | |
| 2010/0209408 A1 | 8/2010 | Stephen et al. | |
| 2011/0065060 A1 | 3/2011 | Teixeira et al. | |
| 2012/0197344 A1 | 8/2012 | Taft et al. | |
| 2012/0269780 A1 | 10/2012 | Marzaro | |

* cited by examiner

*Primary Examiner* — Blaine Lankford
(74) *Attorney, Agent, or Firm* — Oblon, McClelland, Maier & Neustadt, L.L.P.

(57) ABSTRACT

The disclosure is directed to a device and method of treating bone formation disorders or conditions by bioengineering a targeted bone tissue and modulating the homeostasis of osteogenesis and bone resorption by a localized delivery of peripheral blood mononuclear cells and/or hematopoietic stem cells, and/or cells, such as osteoclasts, obtained by the ex vivo differentiation of these cells. A therapeutic strategy, as well as a device to deliver the therapeutic strategy, is described herein.

22 Claims, 14 Drawing Sheets

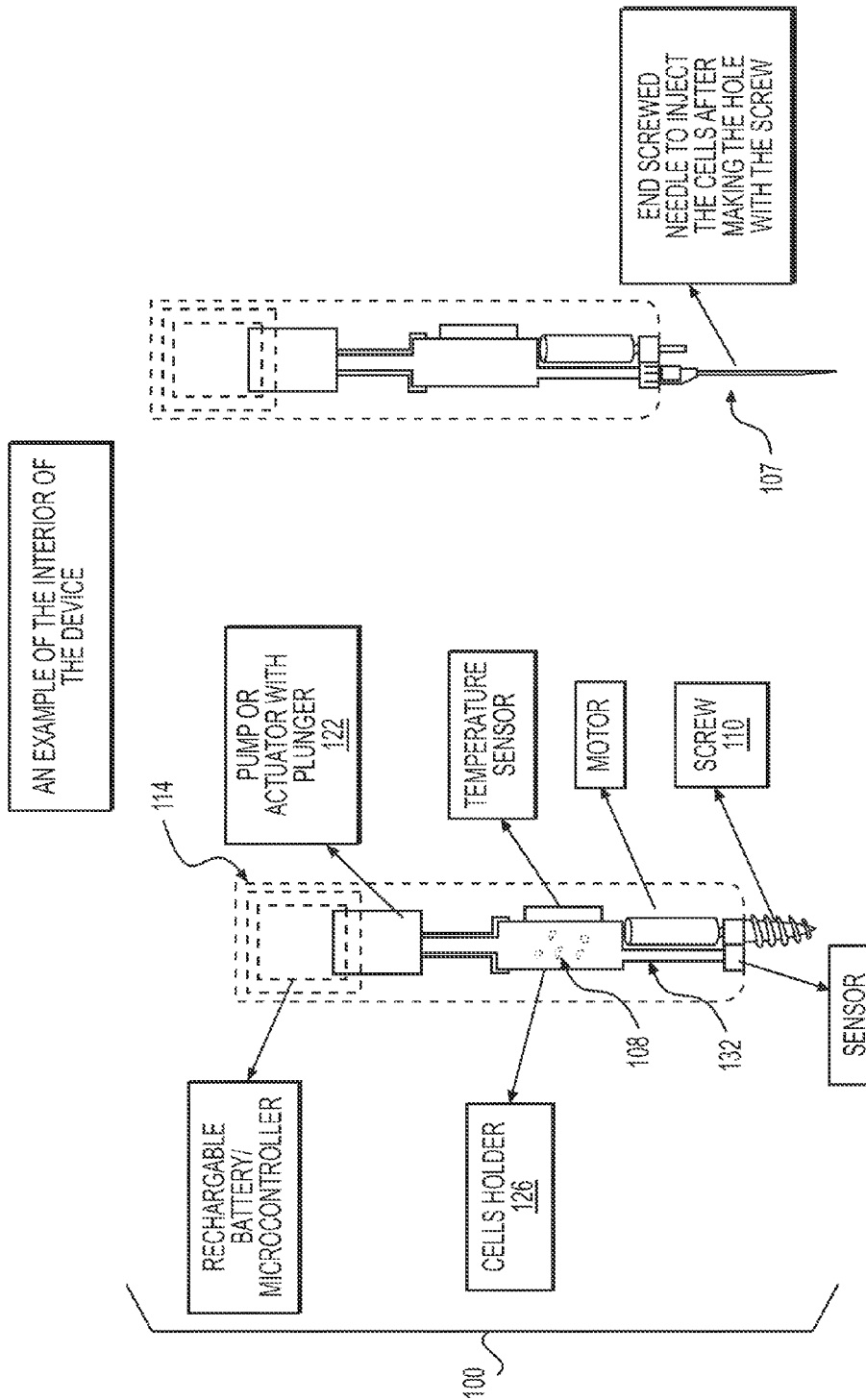

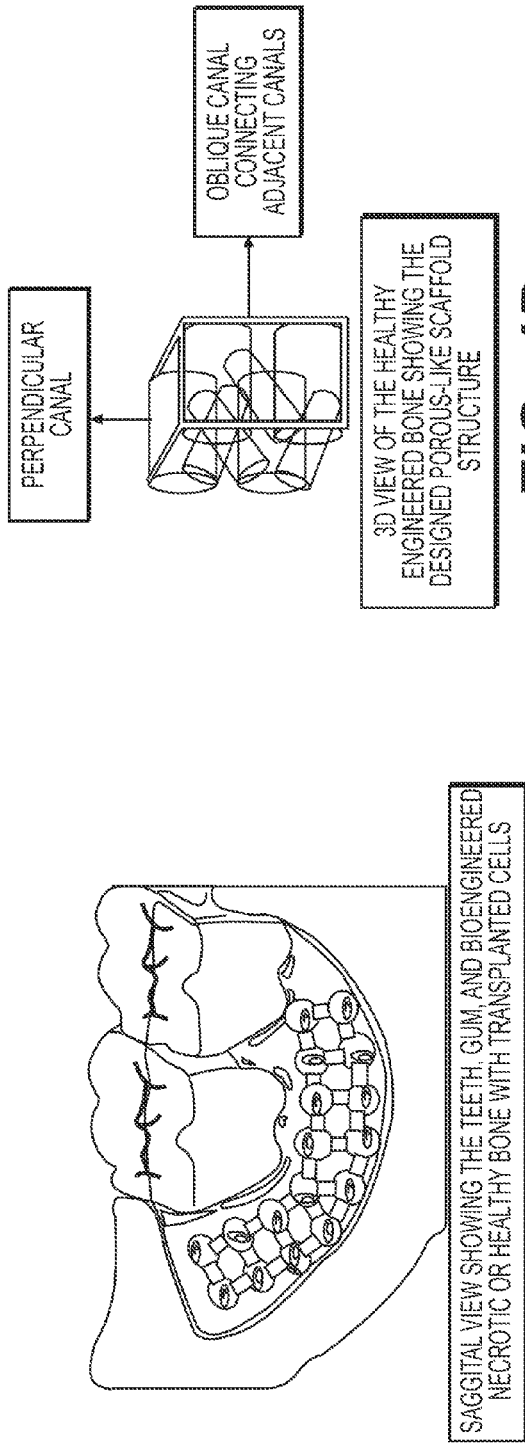

FIG. 4C SAGGITAL VIEW SHOWING THE TEETH, GUM AND BIOENGINEERED NECROTIC OR HEALTHY BONE WITH TRANSPLANTED CELLS

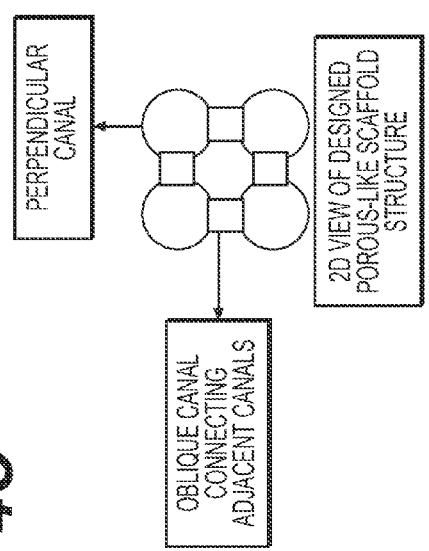

FIG. 4D 3D VIEW OF THE HEALTHY ENGINEERED BONE SHOWING THE DESIGNED POROUS-LIKE SCAFFOLD STRUCTURE (PERPENDICULAR CANAL; OBLIQUE CANAL CONNECTING ADJACENT CANALS)

FIG. 4E 2D VIEW OF DESIGNED POROUS-LIKE SCAFFOLD STRUCTURE (PERPENDICULAR CANAL; OBLIQUE CANAL CONNECTING ADJACENT CANALS)

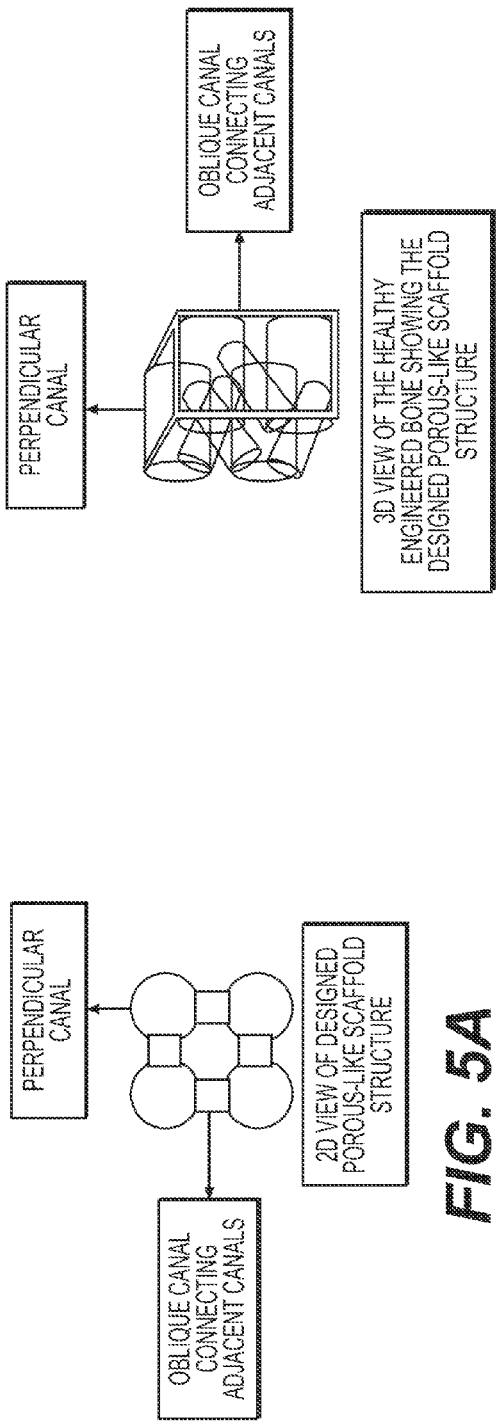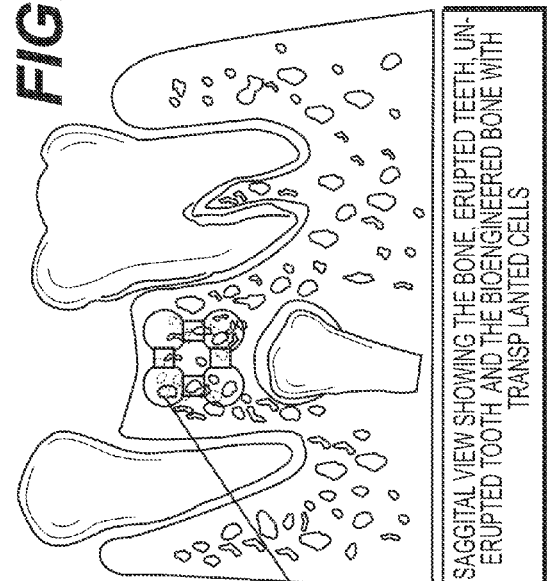

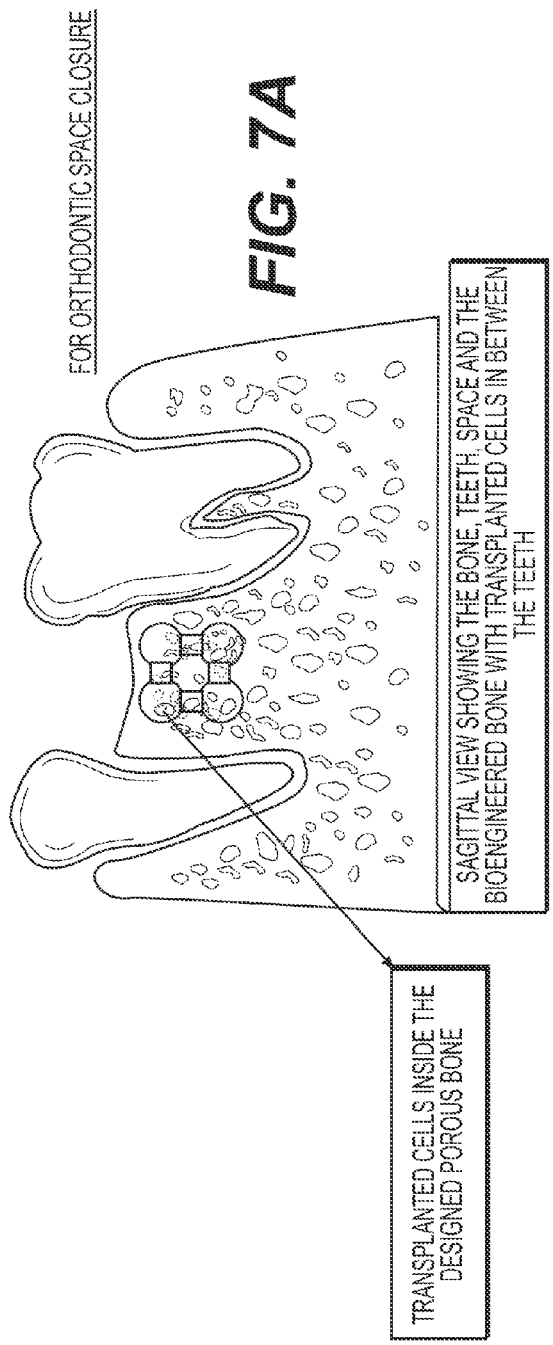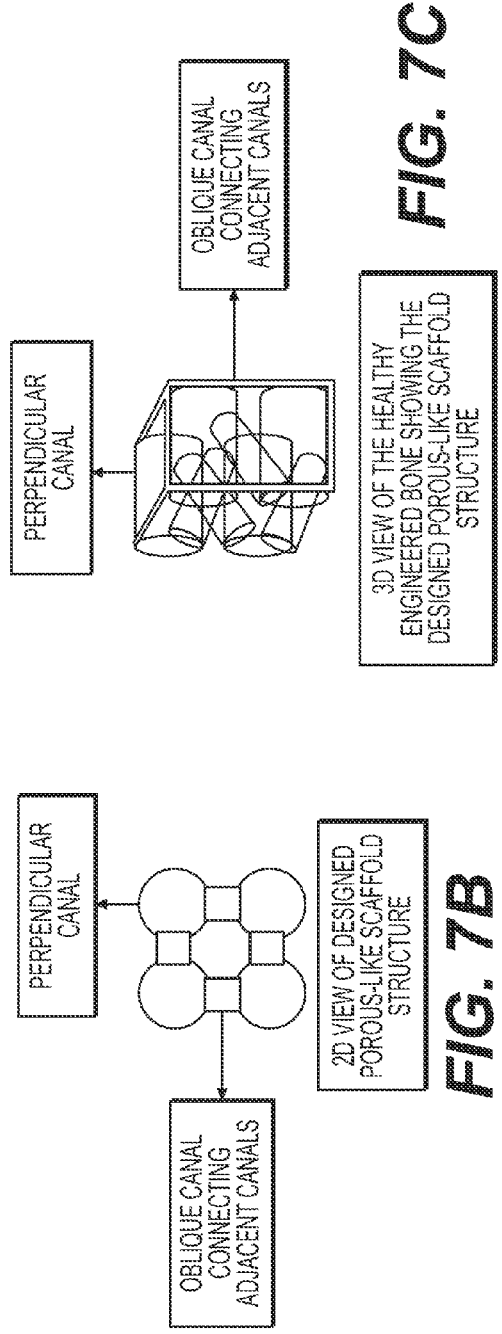

METHOD AND DEVICE FOR BIOENGINEERING BONE TISSUE AND MODULATING THE HOMEOSTASIS OF OSTEOGENESIS

CROSS-REFERENCE TO RELATED APPLICATIONS

U.S. application Ser. No. 13/961,652, filed on Aug. 7, 2013, is incorporated herein by reference in its entirety.

GRANT OF NON-EXCLUSIVE RIGHT

This application was prepared with financial support from the Saudi Arabian Cultural Mission, and in consideration therefore the present inventor(s) has granted The Kingdom of Saudi Arabia a non-exclusive right to practice the present invention.

BACKGROUND

Field of the Disclosure

The present disclosure relates to a method and device for bioengineering a targeted bone tissue and modulating the homeostasis of osteogenesis and bone resorption by a localized delivery of peripheral blood mononuclear cells and/or hematopoietic stem cells, and/or cells, such as osteoclasts, obtained by the ex vivo differentiation of these cells.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Pathological bone conditions are generally classified as belonging to either one of two broad categories comprising excessive bone loss, or excessive bone gain. The mechanism of either excessive bone loss or gain is believed to involve imbalances in the process of bone remodeling. Bone remodeling occurs throughout the lifespan, and involves the erosion and filling of discrete sites on the surfaces of the bones by an organized group of cells. These 'basic multicellular units' as they are known, comprise a group of cells that first dissolve an area of the bone surface and, subsequently, fill it in with new bone. The units consist primarily of osteoclasts, osteoblasts, and their cellular precursors including, but not limited to, monocytes derived from hematopoietic stem cells. In the remodeling cycle, bone is resorbed at the site of an activated unit by osteoclasts, forming a resorption cavity. This cavity is then filled with bone by osteoblasts. Certain factors can delay, prevent, and even reverse, the ossification of bone. This can be accomplished by a decrease in both the number and activation of osteoblasts, as well as an increase in the number and activity of osteoclasts.

Osteoclasts, as members of the 'basic multicellular units', are multinucleated cells that resorb bone tissue. Orthopedic and orthodontic literature confirms that osteoclasts are a key factor in the bone remodeling mechanism. [Miyamoto, T. and T. Suda, Differentiation and function of osteoclasts. Keio J Med, 2003 52(1): p. 1-7. Incorporated herein by reference in its entirety.] Osteoclasts are not simply bone resorbing cells; they also regulate osteoblast function both positively and negatively. [Tatsumi, S., et al., Targeted ablation of osteocytes induces osteoporosis with defective mechanotransduction. Cell Metab, 2007. 5(6): p. 464-75. Incorporated herein by reference in its entirety.] Activation of osteoclasts is generally thought to involve the release of organic acids and membrane-bound enzyme packages onto the surface of the bone. The products of resorption are then taken up via endocytosis for additional intracellular processing within cytoplasmic vacuoles.

Osteoclast-released enzymes involved with the bone remodeling and resorption process are collagenolytic, papain-like cysteine proteases. These include Cathepsin B, C, D, E, G, K and L. Cathepsin K, with optimal enzymatic activity in acidic conditions, is considered the major cathepsin protease involved in the degradation of type I collagen, elastin, and other non-collagenous proteins. Cathepsin K expression is stimulated by inflammatory cytokines that are released after tissue injury. Another osteoclast-released enzyme that appears to be involved in bone matrix degradation is tartrate-resistant acid phosphatase (TRAP). TRAP can dephosphorylate the protein osteopontin, which has been revealed as a key player in anchoring osteoclasts to the mineral matrix of bones. [Reinholt F P, Hultenby K, Oldberg A, Heinegård D (June 1990). "Osteopontin—a possible anchor of osteoclasts to bone". *Proc. Natl. Acad. Sci. U.S.A.* 87 (12): 4473-5. Incorporated herein by reference in its entirety.]

Additionally, hematopoietic stem cells (HSCs) appear to play a greater role in bone maintenance than previously thought. The HSC niche, a particular microenvironment in the bone marrow cavity, has been identified as the controller of a HSC's fate. Notably, active osteoclasts, in addition to osteoblasts, are reasoned to take part in the maintenance of the HSC niche. It is postulated that if the threshold for the minimum required bone marrow cavity space to maintain HSC numbers is exceeded, a reduction in the number of HSC will occur. Osteoclastic bone resorption retracts old osteoblasts from the remodeling endosteal surface and recruits new active matrix producing osteoblasts to the eroded bone surface. Thus inhibition of osteoclast function reduces the rate of osteoblast turnover and may consequently reduce the formation of niche-osteoblasts. A decrease in the number of osteoclasts, or an inhibition of osteoclast function, may result in a reduced number of hematopoietic stem cells (HSCs). [Lymperi S, Ersek A, Ferraro F, Dazzi F, Horwood N, 'Inhibition of osteoclast function reduces hematopoietic stem cell numbers in vivo' (published online Dec. 3, 2010 ahead of print) *Blood* doi: 10.1182/blood-2010-05-282855. Incorporated herein by reference in its entirety.] Also, hematopoietic stem cells (HSC) are known to differentiate into monoblasts that can further differentiate into monocytes. In turn, monocytes can differentiate into a variety of cells including, but not limited to, osteoclasts. It is therefore desirable to have HSCs present in an area that requires osteoclasts, so as to assist in healing a bone wound site that may be cell-poor.

Failure in the production, or metabolic activity, of osteoclasts, mononuclear cells, and/or hematopoietic can lead to a variety of detrimental conditions, as these cells play a significant role in osteogenesis and bone resorption. Bone formation conditions and/or bone disorders linked to an abnormal deposition and/or abnormal turn-over of bone tissues include, but are not limited to, craniosynostosis, hallux abductovalgus abnormalities, osteogenic sarcoma (Osteosarcoma), osteocartilaginous exostosis, ankylosis, osteopetrosis, and osteonecrosis, are briefly outlined below.

Osteopetrosis: This bone condition is known to cause the deformation of the skull and jaw, immature fusion at craniofacial sutures, and failure of tooth eruption. [Kawata, T., et al., Midpalatal suture of osteopetrotic (op/op) mice exhibits immature fusion. Exp Anim, 1998. 47(4): p. 277-81. Incorporated herein by reference in its entirety.] The clinical syndrome osteopetrosis is characterized by the failure of osteoclasts to resorb bone; resulting in systemic bone sclerosis. Three distinctive clinical forms of the genetically inherited disease—infantile, intermediate, and adult onset—are identified based on age and clinical features. As a consequence of this condition, bone modeling and remodeling are impaired, leading to serious skeletal issues. Unexpectedly, skeletal fragility occurs in spite of the increased bone mass associated with osteopetrosis. Clinically, mutations in the cathepsin K gene are believed responsible for pycnodysostosis, a hereditary osteopetrotic disease, characterised by a lack of functional cathepsin K expression. Various treatment protocols have been developed to treat osteopetrosis, for example hematopoietic stem cell and bone marrow systemic transplantation, which is also a prerequisite for normal dental development and eruption of teeth in patients with osteopetrosis. [Jalevik, B., A. Fasth, and G. Dahllof, Dental development after successful treatment of infantile osteopetrosis with bone marrow transplantation. Bone Marrow Transplant, 2002. 29(6): p. 537-40, Steward, C. G., Hematopoietic stem cell transplantation for osteopetrosis. Pediatr Clin North Am, 2010. 57(1): p. 171-80. Incorporated herein by reference in their entirety.]

Craniosynostosis: This bone condition involves the premature ossification of cranial sutures. The term sutures refer to the fibrous joints between the bones in the skull, however sutures are also active growth sites that influence the development, growth and shaping of the face and cranium. Occurring in approximately one of every 2,000 live births, craniosynostosis is characterized by the premature fusion of one or more cranial and/or facial sutures before the brain growth is complete. This premature fusion can cause increased intracranial pressure, resulting in possible impairment of both visual and neurocognitive skills if left untreated. Complex craniosynostosis, involving more than one suture, occurs in approximately 5% to 15% of the cases. At the present time, the only therapeutic measure for craniosynostosis is surgical correction by cranial vault reconstruction. This highly invasive and traumatic procedure involves the reshaping of skull bones and the removal of synostosed bone.

Bunions: Bone disorders or conditions of the first metatarsophalangeal joint encompass a variety of abnormalities. These include hallux abductovalgus abnormalities, otherwise known as bunions. Bunions are boney growths or enlargements of the joint typically found below the toes. While bunions can theoretically occur in any toe, they typically occur in the big toe, (hallux valgus) and occasionally in the little toe. Almost all bunions are related to a combination of a faulty gait, worsened by ill-fitting shoes. The results are an enlargement and deformation of the first metatarsophalangeal joint, which grows new bone tissue to help balance the gait. Once a bunion has formed, the mechanics of the foot and toes are further altered, exacerbating the problem. As a result, pain severe enough to warrant surgery may occur in order to remove the abnormal bony enlargement. This is a costly and painful procedure in which a patient can expect a 6-8 week recovery period.

Osteosarcoma: This is the most common histological form of primary bone cancer. Specifically, it is an aggressive malignant neoplasm which arises from primitive transformed cells of mesenchymal origin that exhibits osteoblastic differentiation and produces malignant osteoid. It is most prevalent in children and young adults. Treatment normally involves a combination of chemotherapy and surgery.

"Cartilaginous exostosis" or "Osteocartilaginous exostosis": These terms are considered by some sources to be synonymous with Osteochondroma, but this interpretation is not universal. An exostosis (plural: exostoses) is the formation of new bone on the surface of a bone, due to excess calcium deposits. Exostoses can cause chronic mild to severe pain depending on the shape, size, and location of the lesion. It is most commonly found in places like the ribs, where small bone growths form, but sometimes larger growths can grow on places like the ankles, knees, shoulders, elbows and hips. Very rarely are they on the skull. They normally form on the joints of bones, and can grow upwards. For example, if an extra bone formed on the ankle, it might grow up to the shin. Complications seen with an exostosis can include fracture, vascular injury, bursa formation, neurologic compromise, and malignant transformation. Treatment for these complications, as well as treatment for those exostoses that are painful or aesthetically unpleasing, is surgery.

Ankylosis: Ankylosis in medical terms is the stiffening or immobility of a joint resulting from disease, trauma, surgery, or bone fusion. Ankylosis occurring in a joint can result in abnormal adhesion and rigidity of the bones of the joint, so that no motion can take place between them. Excision of an ankylosed joint, or area of ankylosed bone, may restore free mobility and usefulness to the corresponding limb.

Ectopic Mineralization: Ectopic mineralization, or etopic calcification, make up a distinct category of abnormal calcium deposition which involves the pathologic deposition of calcium salts in tissues. This can furthermore result in the formation of osseous tissue in such soft tissues as the lungs, eyes, arteries, breast, ovaries, uterus, kidneys and cardiovascular tissues. Cardiovascular concerns include cardiac valve mineralization of both biological and prosthetic heart valves. Treatments for ectopic mineralization conditions are varied.

Osteonecrosis (ON) and Osteonecrosis of the Jaw (ONJ): Osteonecrosis is characterized by the appearance of dead (necrotic) bone forming in various bones of the body. Bones such as the femoral head, and the mandible and/or maxilla of the jaw are common sites for osteonecrosis, and osteonecrosis of the jaw respectively. In many cases, pain and edema of the surrounding tissues accompanies or precedes the development of the necrotic bone. Some forms of ON and ONJ are believed to develop due to a decrease in blood flow to the bone which can occur as a result of a traumatic event, however, there are cases of ON and ONJ which arise due to non-traumatic factors. A percentage of these cases may be termed medication-related osteonecrosis, and are brought about in part by prescription drug use. Medications currently believed to play a role in the development of ON and ONJ include those such as, but not limited to, bisphosphonates, zoledronate, and denosumab. Currently, the pathophysiology of all forms of osteonecrosis and osteonecrosis of the jaw is unknown, although it is believed that many factors contribute to its development. These factors include a compromised immune system, age, corticosteroid use, tissue trauma, Vitamin D deficiency, and the aforementioned medication use. However, how these factors might initially contribute to the development of ON and ONJ is currently unknown, and a topic of great interest. Currently, there are no products available to prevent ON and ONJ. Existing treatments for ON and ONJ are palliative and consist of various protocols which may include a surgical debridement of the necrotic bone—with very limited extension to viable bleeding bone, coupled with analgesic, chlorhexidine rinses and antibiotics. With the majority of minor surgical debridement situations, any tissue death will be repaired by the body. However, with more invasive debridement surgeries comes the undesirable possibility of developing what is termed a 'critical size defect'. The classical definition of a critical size defect is, 'the smallest size tissue defect that will not completely heal over the natural lifetime of an animal'. With regard to bone tissue, any orthotopic defect that the body cannot heal itself, i.e. without medical intervention, is known as a critical size defect. As such, materials or strategies that can cause a complete regeneration of the bone tissue in these defects are highly desired. These may include materials that are considered capable of generating bone at a site and time when bone would otherwise not be present. In many cases, a cosmetic restoration of the area of bone loss with materials considered to bridge non-union defects has been the only available option of treatment to date.

Osteoradionecrosis (ORN): Osteoradionecrosis of the jaw (ORNJ) occurs in subjects receiving radiation treatment, for example, during cancer therapy. It is caused by the radiation that jaw tumor(s) are treated with to eradicate the tumor(s). ORNJ may be managed by increasing local vascularity, and hyperbaric oxygen (HBO) treatment may be an effective option for treating ORNJ by seemingly increasing the formation of new blood vessels.

Further to the function of osteoclasts in bone disorders or conditions, is the role that osteoclasts play in accelerating the rate of tooth movement during orthodontic treatment. Many individuals seek orthodontic treatment to position their teeth where function and/or aesthetics are greatly improved. In order to achieve the desired tooth alignment, bone remolding is necessary, as it is the basis for all orthodontic tooth movement. [Henneman, S., J. W. Von den Hoff, and J. C. Maltha, Mechanobiology of tooth movement. Eur J Orthod, 2008. 30(3): p. 299-306., Xie, R., A. M. Kuijpers-Jagtman, and J. C. Maltha, Osteoclast differentiation during experimental tooth movement by a short-term force application: an immunohistochemical study in rats. Acta Odontol Scand, 2008. 66(5): p. 314-20. Incorporated herein by reference in their entirety.] Conventionally, appliances such as braces have been applied to a patient's teeth by an orthodontist or dentist. The appliance then exerts a continual force on the teeth so as to gradually urge them toward their intended positions. Over time, and with a series of clinical visits to make adjustments to the appliance, the teeth attain their desired alignment.

Primarily, any osteoclast activation during orthodontic treatment is dependent on the orthodontic forces. This activation requires frequent office visits to initially recruit and then sustain a biologically active level of osteoclasts through the application of force placed upon the teeth. Maintaining an elevated concentration of osteoclasts is an important factor in facilitating and accelerating the rate of tooth movement. [Xie, R., A. M. Kuijpers-Jagtman, and J. C. Maltha, Osteoclast differentiation during experimental tooth movement by a short-term force application: an immunohistochemical study in rats. Acta Odontol Scand, 2008. 66(5): p. 314-20. Incorporated herein by reference in its entirety.]

During treatment, orthopedic and orthodontic forces are used as mechanical stimulus to activate the biological response and increase osteoclast activity. The application of additional forces beyond the optimal force magnitude to increase the biological response can lead to a significant injury to the teeth and surrounding tissues either with or without an increase in the biological response. [Yee, J. A., et al., Rate of tooth movement under heavy and light continuous orthodontic forces. Am J Orthod Dentofacial Orthop, 2009. 136(2): p. 150 e1-9; discussion 150-1. Yee, J. A., et al., Rate of tooth movement under heavy and light continuous orthodontic forces. Am J Orthod Dentofacial Orthop, 2009. 136(2): p. 150 e1-9; discussion 150-1. Incorporated herein by reference in their entirety.]. One of the main factors that controls tooth eruption is the activity of osteoclasts, which can delay or accelerate this process.

Further to this process, if a subject is undergoing dentofacial orthopedic treatment, tensile stresses are often employed along a suture to stimulate the growth of different areas in the maxilla, such as the mid palatal suture. The mechanism of this treatment is also stimulated by early osteoclast activation, followed by bone formation.

Although these methods facilitate and accelerate the rate of tooth movement, they still do not meet all of the clinical needs. The limited clinical outcome of these methods may be due in part to the fact that they target osteoclasts indirectly in order to stimulate the biological response, and this is very difficult to achieve.

In orthodontic clinics, patients may begin Phase 1 treatment as early as ages five or six years in order to treat dentofacial bone conditions, otherwise known by the medical term 'malocclusion'. Examples of malocclusions include, but are not limited to, crooked teeth, overbites, and under-bites. The first phase, early treatment, is designed to enable correct biting and chewing, along with guiding the growth of the jaw bones that support the teeth. This is done so as to direct the teeth to come in straight and to direct the jaw bone to grow in the correct alignment. Early treatment also lowers the risk of damage or breakage to protruding, or misaligned, front teeth. Treatment then resumes as a Phase 2 treatment once the patient experiences the eruption of all permanent teeth.

The second phase, traditional braces, is designed to move permanent teeth into their final positions and continue improving tooth function and facial appearance. Both phases can last several years, with treatment time ranging up to ten years in duration.

During the mixed dentition phase of a child, an orthodontist watches for any potential problems with the eruption of the teeth. A delay in the eruption of primary and permanent teeth occurs when a tooth, or teeth, stop erupting and stay in the same place, causing the permanent tooth or teeth to be displaced upon emergence. The delay of the eruption of primary and permanent teeth can have an effect on the growth and development of the jaws and the developing occlusion. Crowding, distortion of the alveolar jaw bone, space loss and distortion of jaw height are some conditions caused by un-erupted teeth.

In other situations, children may experience delays in desired tooth eruption due to the premature loss of deciduous teeth by injury, decay, or any number of underlying genetic causes. For those young subjects who lose baby teeth early, it is desirable to speed up the emergence of the permanent, or adult, teeth so as to provide the child with not only an aesthetically pleasing smile, but a chewing surface which will also serve to prevent any additional tooth loss due to contact withdrawal. Therefore, in treating a delay in tooth eruption it is desirable to target any critical problem first, and to then accelerate the emergence of the adult teeth so as to avoid additional tooth loss in these subjects. With the first phase of orthodontic care involving treating the jaw so as to correct for biting and chewing, commencement of the second phase may be separated by a long period of time while the subject awaits the emergence of their adult teeth. If the length of time from loss of deciduous teeth to emergence of adult teeth is shortened, the second phase treatment could commence in a much more timely manner, thus saving time, and potentially, monetary costs. Therefore, clinical methods that can locally target tooth eruption and increase the speed of treatment (in years) so as to facilitate the progression of this process are desired.

In light of the invasive and traumatic surgical treatments currently used for bone disorders and conditions such as osteonecrosis and osteonecrosis of the jaw, as well as etopic mineralization conditions, and the shortcomings of the orthodontic field in the clinical treatment of dentofacial conditions, it is necessary to find minimally invasive approaches for the treatment of such.

SUMMARY

The disclosure is directed to a method and device for bioengineering a targeted bone tissue and modulating the homeostasis of osteogenesis and bone resorption by a localized delivery of biocompatible compositions comprising a subject's autologous peripheral blood mononuclear cells and/or hematopoietic stem cells and/or cells, such as osteoclasts, obtained by the ex vivo differentiation of these cells. Therapeutic strategies, as well as a device to deliver the therapeutic strategy, are described herein.

In a first embodiment, a method of bioengineering a targeted bone tissue and modulating the homeostasis of osteogenesis and bone resorption in a subject in need thereof comprises:
  obtaining a CT generated scan of a subjects' targeted bone tissue;
  forming a scaffold guide based on the CT generated scan wherein the guide indicates at least four cylindrical cavities locations, angulations and depths to engineer the subjects' targeted bone tissue;
  accessing the site of the subject's targeted bone tissue;
  placing the CT generated guide on or adjacent to the site of the targeted bone tissue;
  drilling into the site of a targeted bone tissue at the locations, angulations and depths indicated on the CT generated guide so as to form a 'scaffold-like' pattern; and
  nucleating at least one of the cylindrical cavities of the scaffold-like pattern with at least one of a subject's autologous cells selected from the group consisting of (a) Peripheral Blood Mononuclear Cells (PBMCs), (b) Osteoclasts derived from PBMCs, (c) Hematopoietic Stem Cells (HSCs) obtained from peripheral blood, (d) Mononuclear cells derived from HSCs obtained from peripheral blood, and (e) Osteoclasts derived from HSCs (mononuclear cells) obtained from peripheral blood;
  wherein the targeted bone tissue is selected from the group consisting of a healthy bone tissue, a bone tissue having a formation condition, and a bone tissue having a disorder.

In a further embodiment, the bone formation condition or bone disorder is selected from the group consisting of a synostotic condition such as synostitic sagittal synostosis, metopic synostosis, lambdoid synostosis, unilateral coronal synostosis, bicoronal synostosis, multiple suture synostosis, and syndromic craniosynostosis.

In a further embodiment the bone disorder is a dentofacial bone disorder such as a malocclusion.

In a further embodiment the bone formation condition or bone disorder is selected from the group consisting of craniosynostosis, a hallux abducto valgus abnormality, osteocartilaginous exostosis, ankylosis, osteogenic sarcoma, and necrotic bone formed as a result of the progression of osteonecrosis, and/or osteoradionecrosis, and/or osteonecrosis of the jaw.

In a further embodiment the bone resorption is at an etopic mineralization condition tissue site comprising soft tissue and the etopic mineralization condition comprises cardiac valve mineralization.

In a further embodiment, the method treats, prevents or delays the progression of the bone condition or bone disorder.

In a further embodiment the method is performed so as to contact only a bone tissue in need of bioengineering In a further embodiment, the method of bioengineering may occur prior to, during, or after a dental surgical treatment.

In a further embodiment the hematopoietic stem cells are induced ex vivo to differentiate into mononuclear cells and/or osteoclasts.

In a further embodiment the mononuclear cells are induced ex vivo to differentiate into osteoclasts.

In a preferred embodiment the PBMCs are induced ex vivo to differentiate into osteoclasts, and the osteoclasts are furthermore disposed in a pharmaceutically acceptable and biocompatible matrix so as to provide a medicament for treating, preventing, or slowing the progression of ON and/or ONJ in a subject.

In a preferred embodiment the hematopoietic stem cells are furthermore disposed in a pharmaceutically acceptable and biocompatible matrix so as to provide a medicament for treating, preventing, or slowing the progression of ON and/or ONJ in a subject.

In a further embodiment, the hematopoietic stem cells are present in the composition in a concentration ranging from 1 cell to 2 million cells, preferably from about 10 cells to 1 million cells, most preferably from about 10 cells to 100 cells.

In a further embodiment, the peripheral blood mononuclear cells are present in the composition in a concentration ranging from 1 cell to 2 million cells, preferably from about 10 cells to 1 million cells, most preferably from about 100 cells to 1,000 cells In a further embodiment, the PBMC-derived osteoclasts and/or HSC-derived osteoclasts are present in the composition in a concentration ranging from 1 cell to 2 million cells, preferably from about 10 cells to 1 million cells, most preferably from about 100 cells to 1,000 cells.

In a further embodiment, the HSC derived mononuclear cells are present in the composition in a concentration ranging from 1 cell to 2 million cells, preferably from about 10 cells to 1 million cells, most preferably from about 100 cells to 1,000 cells In a further embodiment administering the composition results in at least one of increased (i) osteoclasts, (ii) osteopontin (OPN), (iii) activity level of cathepsin K, (iv) activity level of tartrate-resistant acid phosphatase (TRAP), (v) CD34, (vi) CD229, (vii) CD45, (viii) CD150, (ix) CD48, (x) CD244, (xi) RANKL, or (xii) CD14.

In a further embodiment the composition is administered via a pharmaceutically acceptable carrier delivery system selected from the group consisting of a polysaccharide hydrogel matrix, polyethylene glycol, polylactide, polyglycolide, collagen, alginate, agarose, or a combination thereof.

In a further embodiment the composition further comprises at least one of a growth factor, excipient, pH buffer, and antibiotic.

In a preferred embodiment the growth factor is an osteoclastinogenesis inducing growth factor for example but not limited to RANKL.

In a preferred embodiment the growth factor is an angiogenic inducing growth factor selected from the group consisting of vascular endothelial growth factor (VEGF) isomers, and FGF-2.

In a further embodiment said excipient acts as a controlled release component, or a component to increase the residency time of the carrier adhering to bone.

In another embodiment, the present disclosure includes an electronic device for bioengineering a bone tissue comprising:
a first tip configured to penetrate bone,
a second porous, hollow tip configured so as to be interchanged with the first tip configured to penetrate bone, and a handle comprising a distal end and a proximal end, wherein the proximal end comprises a control panel and internal controls;
the distal end comprises a cartridge containing autologous osteoclast cells and/or hematopoietic stem cells and/or mononuclear cells obtained from a subject; and
a plunger configured so as to cause the cells to leave the cartridge and travel through the porous, hollow tip for release into the subject's penetrated bone tissue.

In a further embodiment, the porous hollow tip configured so as to be interchanged is initially held inside the device and resides internal or adjacent to the tip configured to penetrate bone.

In a further embodiment the hollow, porous tip comprises a needle.

In a further embodiment the internal controls are selected from the group consisting of a means for sensing pressure, temperature, speed of penetration of the tip, and time.

In a further embodiment the control panel comprises indicators for the internal controls selected from the group consisting of pressure, temperature, speed and time.

In a further embodiment the device for bioengineering a bone tissue is used in subjects exhibiting a dentofacial bone disorder, an ectopic mineralization condition, a bone formation condition, and/or bone disorder including necrotic bone, so as to cause an increase in bone remodeling.

In a preferred embodiment the necrotic bone is formed as a result of the progression of osteonecrosis, osteoradionecrosis, and/or osteonecrosis of the jaw.

In a further embodiment the device controls and control panel are reusable.

In a further embodiment the osteoclasts and/or mononuclear cells and/or hematopoietic stem cells are held within the cartridge in a carrier delivery system comprising a liquid or gel matrix selected from the group consisting of polyethylene glycol, polylactide, polyglycolide, collagen, alginate, agarose, a polysaccharide hydrogel matrix, or a combination thereof.

In another embodiment, the present disclosure includes a guide for making scaffold like structure in a targeted bone tissue in a subject in need thereof comprising a thin, flexible film capable of recording location and depth markings, wherein said guide is generated from a CT scan of the targeted bone tissue.

In a further embodiment, the thin, flexible film comprises a plastic polymer.

In a further embodiment the guide further comprises a supportive material wherein the supportive material covers an occlusal surface of a tooth, or teeth so as to stabilize the guide during a dentofacial or osteonecrosis of the jaw bioengineering procedure.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3A shows an interior view of the device for the localized administration of the cells of this disclosure with an attached screw tip.

FIG. 3B shows an interior view of the device for the localized administration of the cells of this disclosure with an attached needle tip.

FIG. 4C shows a sagittal view to the teeth, gums and the bioengineered necrotic and/or healthy bone comprising the cell composition as disclosed herein. FIG. 4D shows a 3D view of the healthy engineered bone showing the designed porous-like scaffold. FIG. 4E shows a 2D view of a designed porous-like scaffold structure.

FIG. 5A shows a 2D top view of the cylindrical cavities in a scaffold-like design.

FIG. 5B shows a 3D side view of the cylindrical cavities in a scaffold-like design.

FIG. 6 shows the deposited osteoclast composition inside the targeted bone area for tooth eruption.

FIG. 7A shows the deposited osteoclast composition inside the targeted bone area for orthodontic space closure. FIG. 7B shows a 2D top view of the cylindrical cavities in a scaffold-like design. FIG. 7C shows a 3D side view of the cylindrical cavities in a scaffold-like design.

DETAILED DESCRIPTION OF THE EMBODIMENTS

Figure 1:
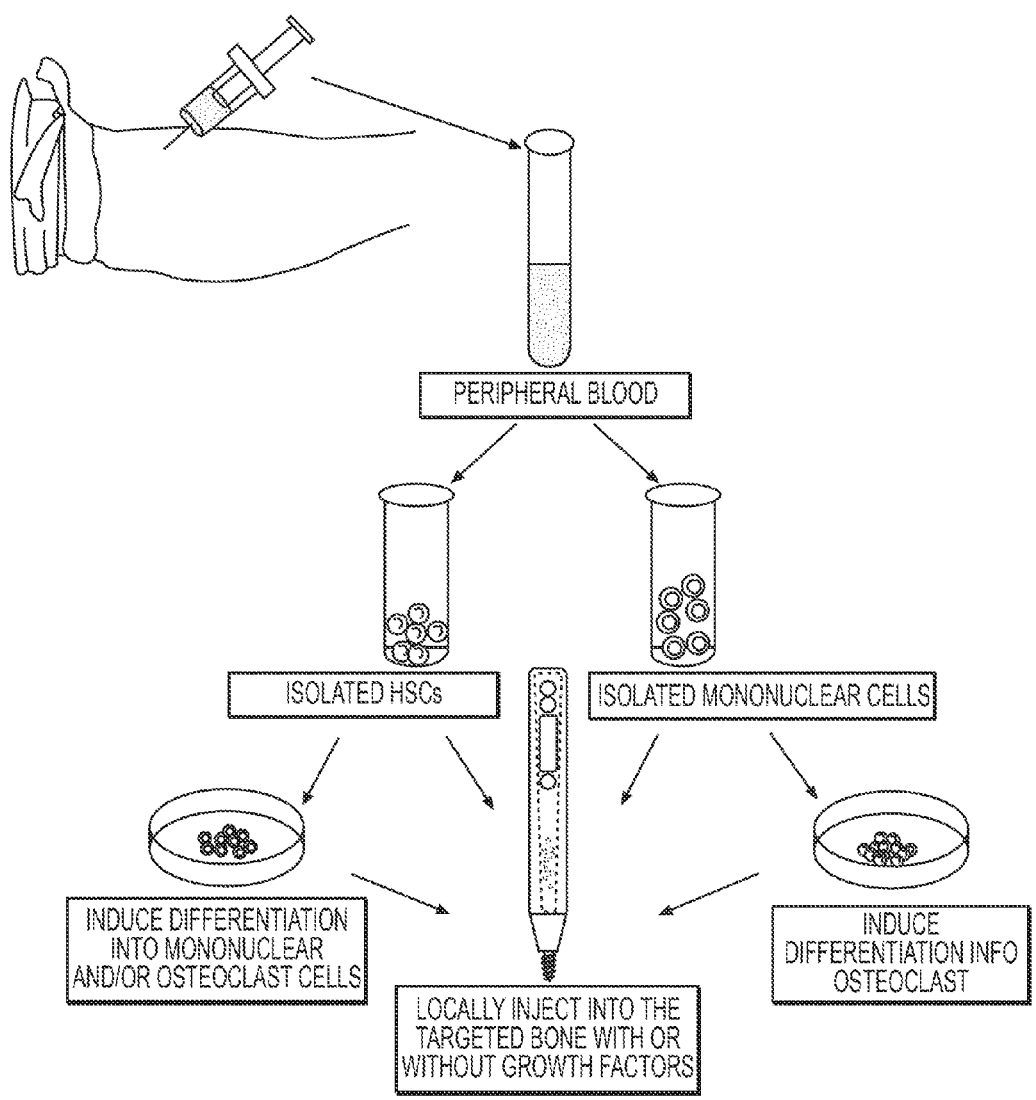
FIG. 1 shows a protocol for obtaining hematopoietic stem cells and/or mononuclear cells and/or osteoclasts derived from these cells from peripheral blood; and a device for localized administration of these cells.

Referring now to the drawings, wherein like reference numerals designate identical or corresponding parts throughout the several views.

Described herein is an approach to modulate the homeostasis of osteogenesis by localized delivery of biocompatible compositions comprising a subject's autologous peripheral blood mononuclear cells and/or hematopoietic stem cells and/or cells, such as mononuclear cells and osteoclasts, obtained by the ex vivo differentiation of these cells to a bioengineered bone site having a scaffold like structure. The approach is based on the activity of these hematopoietic stem cells, mononuclear cells, and osteoclasts, which can affect the ossification of bone, and result in bone remodeling and bone tissue formation.

The scaffold-like structure of the present disclosure is engineered based on 3d ct-scan which allow a predictable bioengineered structure. The cavities on the surface of a bone undergoing treatment may be regularly or irregularly arranged both by location, size, orientation with respect to surrounding structure and to one another and angle of penetration into the affected bone. In one embodiment the cavities forming the scaffold-like structure are arranged regularly such that each cavity is regularly spaced from a neighboring cavity. Such spacing may proceed in one or two regular directions. The depth of penetration may also be regular and/or have periodicity between extremes of the target area undergoing treatment. Preferably the scaffold-like structure is directly on an affected bone surface. The scaffold-like structure may cover the entire affected portion of the bone structure or may cover only a portion. In one embodiment the scaffold-like structure bridges affected and healthy bone structure. In a preferably embodiment such a bridging bone structure provides a conduit by which cells such as osteoclasts may travel fluidly from healthy bone to treated bone through the cavity structure defining the scaffold-like structure of the bioengineered bone described herein. The cavities of the scaffold-like structure may be separated by regular or irregular intervals. In one embodiment cavities are separated by a minimum distance that is defined according to the diameter of the nearest neighboring cavity. For example, at least 90% of the cavities may be spaced at a distance of at least one diameter from the next nearest cavity. In other embodiments cavities that are perpendicularly oriented on the bone structure may at least partially overlap at the surface of the treated bone. The thus-combined cavity may be viewed as a single cavity having a larger total volume than a single cavity but less than the total volume of two separate single cavities.

FIGS. 5A and 5B provide top and side views of the bioengineered scaffold-like structure. In the embodiment shown as a top view in FIG. 5A a set of perpendicularly oriented cavities are connected with a set of angled cavities. The perpendicular cavities are thereby placed in fluid communication either directly or indirectly with one another such that the cell-containing composition can migrate between perpendicular and angled cavities.

FIG. 5B likewise describes an embodiment of the invention as a side view in which the scaffold-like structure has a series of essentially perpendicular canals, i.e., perpendicular to the surface of the bone undergoing treatment, and a series of cavities angled obliquely relative to the perpendicular cavities. The angled cavities serve to connect the spaces within the perpendicularly oriented cavities. The angled cavities may connect 2, 3, 4, 5 or more perpendicular cavities such that the cavities are in fluid communication with one another.

Figure 10A:
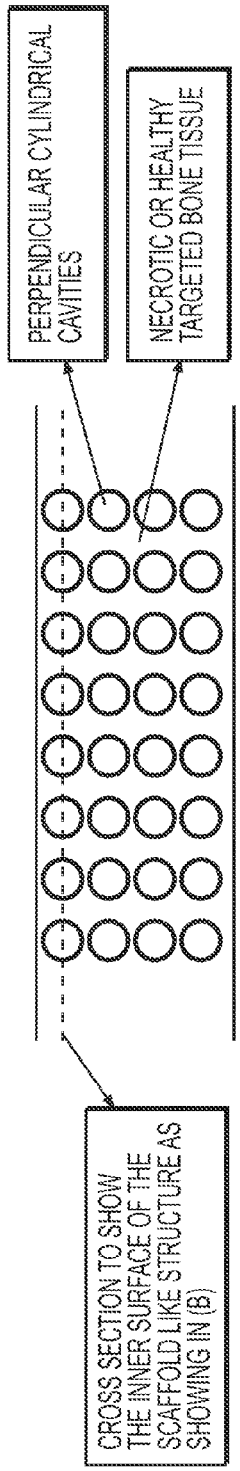
FIGS. 10A, 10B show embodiments of a scaffold like structure and related cavities.
Figure 10B:
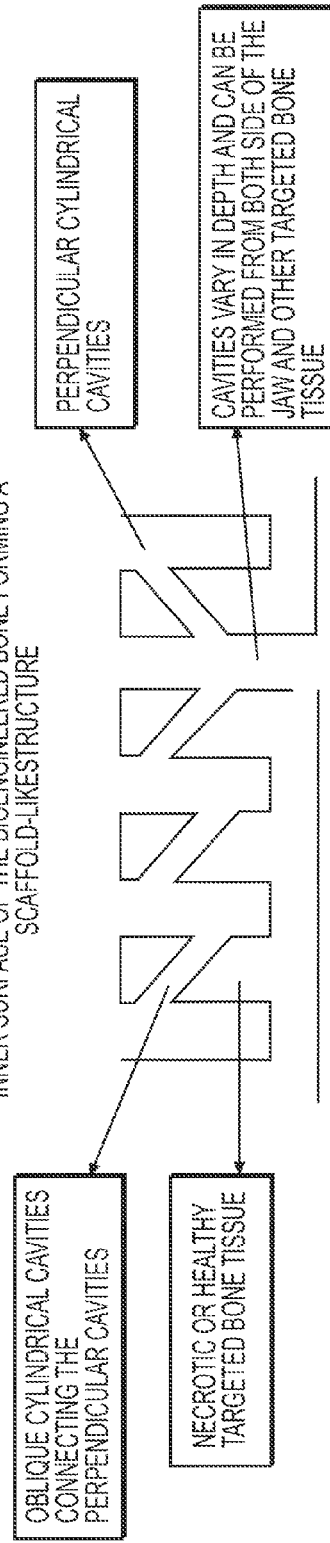

FIG. 10A shows a portion of a bioengineered bone as a cross section. The outer surface of a scaffold like structure is shown. Cavities are oriented perpendicularly to a bone surface. Necrotic or healthy bone tissue may be present between the cavities. FIG. 10B shows a side view of the bioengineered portion of a bone. The side view shows an embodiment in which the perpendicularly oriented cylindrical cavities are connected with one another through angulations. The angulations, or oblique cylindrical cavities, connect perpendicular cavities. Necrotic or healthy bone tissue may exist within the interstices between the perpendicularly oriented cavities and likewise above and/or below the oblique cylindrical cavities. The perpendicularly oriented cavities may vary in depth. Likewise, the angulation of the oblique cylindrical cavities and their point of connection to a perpendicularly oriented cavity may vary. In embodiments of the invention the oblique cylindrical cavity may connect with the perpendicularly oriented cavity at the surface of the bioengineered bone portion.

The disclosure is furthermore directed to a method and device to treat at least one of a bone disorder, bone condition by the introduction of a composition to increase the rate of bone resorption. This method further comprises locally administering at least one of a subject's autologous cells selected from the group consisting of (a) Peripheral Blood Mononuclear Cells (PBMCs), (b) Osteoclasts derived from PBMCs, (c) Hematopoietic Stem Cells (HSCs) obtained from peripheral blood, (d) Mononuclear cells derived from HSCs obtained from peripheral blood, and (e). Osteoclasts derived from HSCs (mononuclear cells) obtained from peripheral blood. Herein this group of autologous cells will be referred to as the "autologous cells" and the "autologous cells of this disclosure". The autologous cells of this disclosure are administered in, at or near areas of a targeted bone tissue through bone resorption and/or bone remodeling at a site that is bioengineered, for example by the provision of a scaffold like structure of cavities. In a most preferred embodiment, the autologous cells are directly introduced into a targeted bone tissue. These areas include the soft tissue, so as to assist tooth eruption and tooth movement during orthodontic treatment, as well as craniofacial areas, including sutures. The sutures may be treated in subjects exhibiting at least one of a synostotic condition selected from the group consisting of synostitic sagittal synostosis, metopic synostosis, lambdoid synostosis, unilateral coronal synostosis, bicoronal synostosis, multiple suture synostosis, and syndromic craniosynostosis. Additional areas for application of the autologous cells of this disclosure are those affected by bone disorders or conditions, including, but not limited to, craniosynostosis, hallux abductovalgus abnormalities, osteogenic sarcoma (Osteosarcoma), osteocartilaginous exostosis, ankylosis, etopic calcifications, and ossification disorders of the mandibular area. It is furthermore postulated that those individuals suffering from ORNJ may also benefit from treatment with these autologous cells. Subjects at risk for ORNJ includes any patient in need of or already receiving radiation treatment of the mandible, maxilla or surrounding tissue and bone.

The cells may be contacted, injected or delivered with bone that is not covered by soft tissue, or on other aspects of the invention the cells are contacted, injected or delivered to bone that is present under soft tissue. In one aspect soft tissue can be separated from bone, cells administered to a scaffold-like structure bioengineered to a bone site, and then the tissue reconnected or used to cover the target site.

It is also within the scope of this disclosure that osteoclasts may be obtained from peripheral blood mononuclear cells genetically modified to produce osteoclasts expressing normal cathepsin K, for use in treating individuals diagnosed with conditions of osteopetrosis.

The treatment disclosed can be administered preemptively, post-pathologically, or both, to treat the bone disorders or conditions. The ability to treat these disorders with an autologous cell type can provide reduced cost, increased convenience, and reduced toxicity, as well as providing an immuno-compatible alternative treatment. A determination of need for the treatment can be assessed by a subject's medical history and physical examination(s) consistent with one of the above bone disorders, bone conditions, or etopic mineralization. Subjects of said disclosure are preferably human, but may also include mammals, such as horses, cows, dogs, cats, sheep, and pigs. Subjects who would benefit from the methods of this disclosure include those with a diagnosed condition described herein or indication of a condition amenable to therapeutic treatment described herein, and subjects who have been previously treated, are being treated, or will be treated for such conditions.

The method of this disclosure may further comprise the isolation of a subject's peripheral blood mononuclear cells and/or hematopoietic stem cells and an optional subsequent inducement ex vivo to cause these cells to differentiate into active osteoclasts. A device as disclosed herein is then used to locally administer the autologous cells of this disclosure to an area in need of bone treatment, preferably with bioengineering, such as bone remodeling.

Osteoclasts develop by the fusion of mononuclear precursor cells of the monocyte-macrophage lineage in the presence of the osteogenetic cytokines, for example macrophage-colony stimulating factor (M-CSF) and receptor activator of nuclear factor-jB ligand (RANKL). Osteoclasts can be generated from human peripheral blood, bone marrow, or any part of the body where hematopoietic cells can be obtained. Herein, the term biological sample is a blood sample or serum or tissue extract sample comprising an osteoclast precursor, such as peripheral blood mononuclear cells.

According to a preferred embodiment, a blood sample provides peripheral blood mononuclear cells (PBMCs). These PBMCs can be isolated from approximately 50 mls of blood by Ficoll-Hypaque gradient. [Boyum, Scand J Clin Lab Invest Suppl 1968; 97: 77-89. Incorporated herein by reference in its entirety.] The number of CD14+ osteoclast precursors can be determined by a fluorescence activated cell sorter (FACS).

Provided herein is an ex vivo culturing protocol for the differentiation of human stem cells into osteocytes. Such cells can be isolated, purified, and or cultured by a variety of means known in the art. For example, following the isolation of PBMCs as described above, the whole population of PBMCs can be cultured under differentiating conditions for 21 days in the presence of recombinant RANKL (75 ng/ml) and M-CSF (10 ng/ml) fixed, stained for TRAP (Tartrate Resistant Acid Phosphatase 5$b$) activity and for hematoxylin. The number of TRAP+ cells containing three or more nuclei can be counted in each well [Durand M, Gallant M A, de Brum-Fernandes A J., "Prostaglandin D2 receptors control osteoclastogenesis and the activity of human osteoclasts", J Bone Miner Res. 2008 July; 23(7):1097-10 Incorporated by reference in its entirety].

In another exemplary protocol, osteoclasts are generated from human peripheral blood, with the mononuclear cells of interest undergoing isolation by centrifugation over a Lymphoprep gradient. Said cells are then seeded into a Petri dish containing aMEM (Sigma) supplemented with 10% calf serum (FCS; Thermo Fisher, Geel, Belgium), 2 mM L-glutamine, 20 ng/mL M-CSF (R&D Systems, Wiesbaden-Nordenstadt, Germany), and 30 lg/mL gentamycin. This results in a pure pre-osteoclastic cell culture with no contamination by other cell populations. After approximately 10 days in culture (pre-culture), adherent cells are removed using trypsin and experimental cells were seeded into 48-well plates containing bone or dentin slices at a density of 7.2 9 104 cells/cm2 in alpha MEM supplemented with 10% FCS, 2 mM L-glutamine, 30 lg/mL gentamycin, 20 ng/mL M-CSF, and 2 ng/mL RANKL (R&D Systems, Wiesbaden-Nordenstadt, Germany). Culture medium was changed twice per week [Rumpler, M., et al., Osteoclasts on bone and dentin in vitro: mechanism of trail formation and comparison of resorption behavior. Calcif Tissue Int, 2013. 93(6): p. 526-39. Incorporated herein by reference in its entirety].

Concurrent with the administration of the PMBC osteoclasts a second HSC and/or mononuclear cell component may be administered. Hematopoietic stem cells are blood stem cells derived from the bone marrow, blood (such as peripheral blood and umbilical cord blood), or amniotic fluid. Collecting peripheral blood stem cells provides a greater amount of cells as compared to those cells obtained from bone marrow, does not require that the subject undergo general anesthesia to collect the cells, and is much less invasive. Mononuclear cell precursors of the human osteoclasts have also been identified in both bone marrow and the circulation. [Human osteoclast formation from blood monocytes, peritoneal macrophages, and bone marrow cells. Quinn J M, Neale S, Fujikawa Y, McGee J O, Athanasou N A. www.ncbi.nlm.nih.gov/pubmed. Incorporated herein by reference in its entirety.]

For the bone disorders and conditions described herein, co-administration of an osteocyte and hematopoietic stem cell-containing therapeutic composition is compelling. The addition of HSCs has the potential to increase the quantity of cells recruited to a bone healing site, and this enrichment in the number of cells can cause the formation of a healing blastema. Many subjects who have undergone long term bisphosphonate treatment, which significantly reduces the number and activity of the cell population necessary for bone healing, would greatly benefit from this therapeutic composition.

The quantity of the osteoclast/HSC/mononuclear cell-containing composition to be administered may be determined by the bone volume that is surgically removed, or drilled, for example from an extraction socket, a cystrectomy, a necrotic bone tissue, or during periodontal bone surgery.

As a preventative treatment, the administration of the osteoclasts and/or HSCs and/or mononuclear cells obtained from said subject's peripheral blood mononuclear cells induced ex vivo to differentiate into said osteoclasts, (PBMC osteoclasts) is also appropriate for a patient population at risk for developing ON and ONJ. The preventative treatment emphasizes prophylaxis, which comprises co-administration of the osteoclast and/or HSCs and/or mononuclear cell containing composition concurrently with any dental procedure. For example, a patient at risk and having a dental surgical procedure such as an extraction may have the cell-containing composition, in one embodiment, co-administered with, for example, a dental extraction medicament or dressing.

Similarity, the use of the PBMC osteoclasts/HSCs/Mononuclear cells in an oro-dental cystrectomy, wherein the cell-containing composition is placed into the cystic cavity. Still another example includes a periodontal procedure where gingival tissues are incised and alveolar and/or interradicular osseo-dental surgery are performed and the cell-containing composition is co-administered with the periodontal therapy dressing.

As previously stated, those subjects at risk for ONJ includes any patient taking oral or intravenous bisphosphonates in need of dental surgical treatment, especially those procedures considered more invasive or traumatic including but not limited to, dental implant procedures, tooth extractions and periodontal surgery. As a course of prevention or treatment, these subjects receive PBMC-derived osteoclasts in a pharmaceutically acceptable carrier prophylactically at the treatment sites to prevent the occurrence of ONJ. Administration may occur prior to, during, or after said dental surgical treatment.

The autologous cell composition of this disclosure, being capable of attenuating ossification, can be administered via a carrier delivery system. The carrier delivery system can be a liquid or gel matrix, depending on the desired delivery preferences. The carrier material can contain, be coated with, or infused with such HSC/osteoclast/mononuclear cells. The autologous cell composition can be made available in immediate release formulations, sustained release formulations, or both. One of skill in the art could determine whether a subject would most benefit from an immediate release formulation or a sustained release formulation based on factors such as the subject's age, gender, ethnicity, degree of bone disorder or condition, health status, vitamin D status, blood calcium levels, parathyroid levels, and physical activity.

Immediate release formulations include liquid formulations comprising at least osteoclasts, which are applied to the target area. The liquid formulations deliver the osteoclasts in a bioavailable form to a targeted site at rates dictated by the fluid properties of the liquid formulation. These rates include diffusion rates at the site of the local administration. Examples of suitable liquid formulations comprise fluid mediums that will not induce host immune responses. These include, but are not limited to, such fluid mediums as water, saline, and Ringer's solution. Additionally, liquid polymer systems may also be employed wherein said liquid compositions may be introduced into the body of a subject in liquid form, the liquid composition then solidifies or coagulates in situ to form a controlled release implant, and the osteoclasts are then released into the surrounding tissue.

Examples of suitable carriers include polymeric delivery systems which can include biodegradable polymer materials. Such a delivery system may be selected from the group consisting of, but not limited to, a polysaccharide hydrogel matrix, polyethylene glycol, polylactide, polyglycolide, polyanhydrides, collagen, alginate, agarose, or a combination thereof. These illustrate varying levels of controllable degradation rates for tailoring the delivery of said osteoclasts to the targeted area in need of bone resorption.

Encapsulated autologous HSC/osteoclast/mononuclear cell compositions can provide greater controlled release over extended periods of time. If desired, encapsulation of the cells can be carried out via a water-oil single emulsion method or a water-oil-water double emulsion method.

It is also recognized that the osteocytes need to reside at the sites of defect long enough to attenuate the selected ossification, and preferably should not seep nor migrate to surrounding areas where normal bone growth is observed. Excipients can be added to the delivery system to stabilize the liquid or gel matrix during assembly in order to impact the osteoclast release rate. Such excipients include, but are not limited to, mucoadhesive polymers such as chitosan and hydroxypropylcellulose. These can increase the residency time of the carriers system containing the osteoclasts adhering to the bone. Additional excipients can be added to the carrier delivery system to stabilizer the emulsion during the encapsulation process.

Summarily, suitable formulations allow for the measured release of the autologous cells into the selected target area so as to deliver the bioactive cells at a rate which best meets the bone remodeling needs of the subject. However, the duration of release from a sustained release formulation can also be influenced by biological factors such as blood flow and heat to the targeted tissue site.

The agents described herein can be formulated by any conventional manner using one or more pharmaceutically acceptable carriers and/or excipients as described above. Such formulation will contain a therapeutically effective amount of osteoclasts and/or HSCs and/or mononuclear cells, together with a suitable amount of carrier, so as to provide the form for proper administration to a subject.

Compositions may optionally include one or more antibiotics that may be co-administered so as to prevent infection by obligate or opportunistic pathogens that may unintentionally be introduced to the subject during the localized treatment. Antibiotics include, but are not limited to, those treating gram positive, as well as gram negative bacteria. Said antibiotics include, but are not limited to, those from the classes of cephalosporins, tetracyclins, macrolides, glycopeptides, quinolones, and oxazolidinones. Additionally, silver nanoparticles may be incorporated in the gel matrix in order to impart anti-pathogenic properties.

Compositions should also include a growth factor such as osteoclastogenic, osteogenic, and/or angiogenic inducing growth factor.

Further additives include those necessary to maintain a stable isotonic environment for the cells. These additives include, but are not limited to, water, saline, Ringer's solution, and dextrose.

As cathepsin K has optimal enzymatic activity in acidic environments, a pH buffering system may be added so as to maintain the ability of cathepsin K to function at its greatest enzymatic activity level. Buffering systems may include, but are not limited to, those such as the bicarbonate and phosphate buffering systems.

Most advantageously, there is no need to include immunosuppressive agents into the formulations due to the benefit of the osteoclasts and/or HSCs and/or mononuclear cells being obtained from the patient's own peripheral blood.

Administration sites for orthodontic use include subgingival, subperiosteal, and/or transligamentary (periodontal ligament) sites occurring around the teeth, or sutures. Administration sites for the treatment of synostotic conditions selected from the group consisting of synostitic sagittal synostosis, metopic synostosis, lambdoid synostosis, unilateral coronal synostosis, bicoronal synostosis, multiple suture synostoses, and syndromic craniosynostosis occur at the juncture of the aforementioned cranial sutures.

In one embodiment the administration site is covered with soft tissue such as gum. The osteoclasts and/or HSCs and/or mononuclear cells may be administered to a underlying bone tissue layer by penetrating the soft tissue layer or by first separating the soft tissue layer from the bone layer. In a preferred embodiment the soft tissue layer is separated from the bone tissue prior to administration of the osteoclasts and/or HSCs and/or mononuclear cells. Subsequent to administration of the osteoclasts and/or HSCs and/or mononuclear cells the soft tissue may be reconnected by suture or other physical means to the bone site by contact with neighboring soft tissue. More preferably the soft tissue is separated from the bone to form a flap that can be returned to the targeted bone site and placed over the bone tissue to which the osteoclasts and/or HSCs and/or mononuclear cells have been administered. Alternately the osteoclasts and/or HSCs and/or mononuclear cells can be administered to a bone site by concurrently penetrating a soft tissue layer and a bone layer with the tool disclosed herein and then dispensing the osteoclasts and/or HSCs and/or mononuclear cells at or in the targeted bone tissue.

Administration sites for the treatment of a bunion, an osteocartilaginous exostosis, an osteogenic sarcoma, or an etopic mineralization condition occur at the location of said abnormality or formation.

Administration of said osteoclasts initially comprises accessing a site of intended autologous cell delivery. Preferably, accessing the site is performed in a minimally invasive manner. However, the method of the disclosure may make use of any suitable means of accessing the bone defect including traditional, more invasive methods known to one of skill in the art. It is also foreseen that the methods described herein can be performed in conjunction with conventional surgical techniques for the treatment of the bone conditions and disorders herein described. Administration of an effective amount of the autologous cell composition will generally increase osteoclast numbers and/or osteoclast activation and/or osteogenic differentiation so as to delay or reduce the ossification of bone or increase the resorption of bone in the site in need of bioengineering. Administration may also result in an increase in activity of cathepsin K and/or activity of tartrate-resistant acid phosphatase (TRAP) and/or levels of osteopontin protein (OPN) so as to delay or reduce the ossification of bone or increase the resorption of bone in the site in need of bone remodeling.

A computed tomography scan, or the like, can be used to provide a three-dimensional (3D) image of a targeted bone tissue. The treatment of a site of the targeted bone comprises accessing this site, and in one embodiment, an incision is made so as to form a flap of skin and/or muscle tissue(s) and concurrently expose the targeted bone tissue. A scaffold like structure guide may be generated from the 3D image and indicates the placement, angulation, and depth of the cylindrical cavities to be made on or into the targeted bone tissue. In one embodiment, the guide is placed on or adjacent to the exposed bone tissue. The guide directs the drilling of the cylindrical cavities so as to form a scaffold like pattern comprising substantially cylindrical cavities of a diameter of 1 mm-5 mm, preferably 2-4 mm or about 3 mm. Drilling of the cylindrical cavities may occur using an electronic screw-tipped device as disclosed herein, or by other means known in the art. The bone cylindrical cavities as formed by drilling range in number from 2 to 1000 cylindrical cavities per area in need of treatment. In a preferred embodiment, the number of cylindrical cavities range from 2 to 50 cylindrical cavities per target bone tissue area, preferably from 8 to 18 or 5 to 13 cylindrical cavities, but may be any number, preferably more than 1 such as 2, 3, 4, 5, 6, 7, 8, 9, or 10, or any multiple of 2, 3, 4, 5, 6, 7, 8, 9, or 10 of thereof. The cylindrical cavities may be 0.10 mm to 5.00 mm in diameter, preferably 0.5 mm-4.00 mm, 1.0-4.0 mm, or 2.50 mm-3.50 mm in diameter. The cylindrical cavities may range in depth from 7 mm-50.00 mm deep, 7 mm-10.00 mm deep, 7.5 mm-9.2 mm deep, 7.8 mm-8.00 mm deep, and occur so as to form a scaffold-like network of cylindrical cavities. This scaffold-like network is conformed so as to allow the greatest level of bone rebuilding and renewal. Bone in this area may re-form so as to not leave any voids, or cavities, in the bone tissue. The cylindrical cavities may also be made so as to pass into or penetrate any of the medullary cavity, periosteum, endosteum and/or compact bone.

The guide that is formed with the CT scan serves three important purposes including: identifying the location where one or more cavities should be placed, identifying the depth of the cavity, and identifying the angulation of a cavity intended to crosslink or join cavities that are oriented perpendicular to a bone surface. By providing this information and guidance the guide permits appropriate and correct location and position of the cavities to obtain improved bone regeneration or bone regrowth capability and avoid any injury to the surrounding structures.

Furthermore the process may include the nucleating at least one of the cylindrical cavities of the scaffold-like pattern with at least one of a subject's autologous cells selected from the group consisting of (a) Peripheral Blood Mononuclear Cells (PBMCs), (b) Osteoclasts derived from PBMCs, (c) Hematopoietic Stem Cells (HSCs) obtained from peripheral blood, (d) Mononuclear cells derived from HSCs obtained from peripheral blood, and (e) Osteoclasts derived from HSCs (mononuclear cells) obtained from peripheral blood.

The amount of osteoclasts and/or HSCs and/or Mononuclear cells in a carrier delivery system that may be included in a single dosage form will vary depending upon the subject being treated and the particular mode of administration. An individual dose of each individually tailored dosage need not in itself constitute a therapeutically effective amount, as the necessary therapeutically effective amount could be reached by administration of a number of individual doses. Autologous cell administration can occur as a single event, or over a time course of treatment. In a preferred embodiment, the autologous cell/carrier delivery system can be administered daily, weekly, bi-weekly, or monthly during the course of treatment. The course of the treatment may extend from one treatment administered one time to many treatments administered at varying frequency over 36 months in time.

Subsequent to any administration of the formulation, targeted bone tissue may receive one or more follow up-treatments selected from the group consisting of, but not limited to, heat and/or ice, increased pressure, and increased tension, including braces to move the teeth.

The specific therapeutically effective dose level for any particular subject will depend upon a variety of factors previously noted herein, including the condition being treated, the severity of the condition. Further to the subject themselves, the age, gender, ethnicity, exposure to sunshine, Vitamin D status, blood calcium levels, parathyroid levels, body weight, physical activity, and general health a will be considered.

Toxicity and therapeutic efficacy of such formulations can be determined by standard pharmaceutical procedures in cell cultures and/or experimental animals for determining the $LD_{50}$ (the dose which is lethal to 50% of the population) and the $ED_{50}$ (the dose which is therapeutically effective in 50% of the population). The dose ratio between toxic and therapeutic effects is the therapeutic index that can be expressed as the ratio $LD_{50}/ED_{50}$ where large therapeutic indices are preferred.

Subjects may range in age from 2.5 to 95 years old. Gender considerations are notable in that fluctuating hormonal levels in women affect bone mineralization. Additionally, those individuals with greater exposure to sunlight and/or greater Vitamin D levels, and/or physical impact activities may have denser bones and require a more aggressive treatment involving a greater number and depth of cylindrical cavities, as well as an increase in the number of osteoclasts delivered.

Any further pharmaceutical treatments in combination or coincidental with the specified osteoclast/carrier delivery system employed will also be under consideration. Agents or devices that assist in bone resorption or bone remodeling can also be used in combination with the therapeutic modalities of this disclosure. Thus in addition to the therapies described herein, one may also provide to the subject other therapies known to be efficacious for particular bone formation conditions or bone disorders, or ectopic mineralization. In a preferred embodiment, the use of braces, or other orthodontic devices, is used in combination with the delivery of the osteoclast matrix.

It is desirable that the depth of the cylindrical cavities and the number of multiple cylindrical cavities is kept to a minimum so as to be more comfortable for the subject, reduce the risk of infection of said subject, and require much less recovery time.

The cylindrical cavities of this disclosure are made so as to pass into one or more of the medullary cavity, the periosteum, the endosteum and/or compact bone of a subject. The cylindrical cavities of this disclosure are preferably made so as to penetrate through the compact bone and preferably to avoid contact with the medulla, or medullary cavity of the bone tissue undergoing treatment. The cylindrical cavities distance, angulation and depth may vary within the area undergoing treatment so as to tailor said treatment to said specific area. For example, thinner, more porous bone having a fewer number of cylindrical cavities made at a lesser depth while thicker, more dense bone having a greater number of cylindrical cavities made at a greater depth. The cylindrical cavities of this disclosure will be made in designed manner into said tissue in need of a bone remodeling or resorption treatment.

Such cylindrical cavities are not sufficient to enhance the bone remodeling process and subsequently accelerate bone resorption. Therefore, in a preferred embodiment said cylindrical cavities, coupled with the injection of the osteoclast/carrier delivery system, are sufficient to accelerate tooth movement. During or immediately following the formation of said cylindrical cavities, the autologous cell composition of the disclosure is released at, into, or near the site of said cylindrical cavities, so as to achieve contact with said bone tissue. In a most preferred embodiment, the autologous cell composition is deposited into the site of the cylindrical cavities.

Subsequently, a perio dressing and/or a periodontal dressing may be placed in or on the area of the engineered bone, once the osteoclast or cells matrix has been released. When said cylindrical cavities involve the oral cavity, a perio dressing and/or a periodontal dressing is preferably employed so as to assure that the osteoclast and/or cells matrix remains on site for an extended time. Further use of a chemical antiseptic and/or anesthetic at the site of the engineered bone is preferred; either prior to, during or immediately after said cylindrical cavities are formed in order to minimize the subject's risk of infection and discomfort. The perio dressing and/or periodontal dressing functions to maintain close contact between a soft tissue flap and a bone layer or to cover the punctured tissues. Curing compositions may be used to form a dressing having mechanical attributes favorable to maintaining a shape and holding pattern of a flap to underlying bone.

The further use of a heat or cold applied to the area undergoing bone remodeling will assist in the process, and can be attenuated to either increase or decrease the activity of the osteoclasts administered to said site.

With the exception of treating ectopic mineralization, the method of administration comprises creating cylindrical cavities in the skull, foot, oral cavity or other area of the subject's body in need of bone resorption, including such areas as those exhibiting ankylosis or osteosarcoma.

In a preferred embodiment the method utilizes a device to make a small cavity, or hole in bone with a low speed electric motor, or manually. The device is used to form the scaffold like structure. The device comprises a tip, which can vary in size and shape based on the area of the transplantation, to administer the osteoclasts. The tips also provide a suitable structure to drill into the bone. Suitable tips include those with a screw, bur or needle-like structure. Said tip must be porous to allow the deposition or injection of said osteoclast or cells matrix. Cylindrical cavities formed there though vary in number from 2 to 1000 and also vary in diameter from 0.10 mm to 5.00 mm. The density in numbers, angulation and the size of injection cylindrical cavities for administration of said osteoclasts also influence the rate of release of osteoclasts to the surrounding targeted area.

In a preferred embodiment, the tip of the device, in addition to being porous, also exhibits markers, or stops, to indicate various drilling depths.

FIG. 2A shows the exterior of the cell transplantation device 100 for injecting a prepared osteoclast and/or cells matrix 108 into a tissue in need of bone remodeling or bone resorption. The device 100 allows for the drilling of a small cylindrical cavities for the insertion of the osteoclast and/or cells matrix 108. The device has a control button 102 for the cells matrix injection and an informatics screen 104 for displaying parameters such as, but not limited to, temperature, speed of drilling, angulation, depth of drilling, and battery. An adjacent control button 106 controls the motor (not shown) for the device 100. An internal cell cartridge provides a temperature insulated storage area for said osteoclast/carrier delivery system 108. The cell cartridge is designed to hold multiple dosages of the osteoclast/carrier delivery system for injection into the so formed cylindrical cavities. A screw tip 110 with small holes 112 allows for the controlled release/injection of the osteoclast matrix 108 either during the drilling process, or after the drilling process is complete. In a preferred embodiment, the screw tip 110 also includes markers, or stops, to indicate drilling depths.

When administering the osteoclast/carrier delivery system, care is taken so that only that tissue in need of remodeling or resorption is contacted with said osteoclast/carrier delivery system.

The device further comprises an internal cartridge to hold the osteoclasts either embedded in, encapsulated in, or adhered to, the carrier delivery system. The internal cartridge can be made from any material which limits temperature fluctuations so as to avoid any increase of temperature during the procedure, which may detrimentally affect cells activity and viability. In some embodiments, an ectopic mineralization condition or disorder, such as ectopic calcification, is treated by accessing a tissue site in need of treatment in the subject, preferably with minimally invasive means, and administering a biologically active amount of said osteoclast/carrier delivery system. The preferred embodiment of the device to treat ectopic mineralization incorporates a needle-like tip for administration of the osteoclasts to said site of the ectopic mineralization or ectopic calcification.

FIG. 6 describes a bone tissue having a scaffold-like structure and including transplanted cells. The scaffold-like structure is demonstrated as a top view showing that larger cavities perpendicularly oriented to the surface of the bone are interconnected by a set of obliquely angled cavities. The cavity space defined by the perpendicularly oriented cavities is in fluid communication with the cavity space defined by the obliquely angled cavities. Such systems of interconnected cavities are reproduced throughout the portion of the bone having a scaffold-like structure produced by bioengineering. In FIG. 6 the cell composition is placed in a portion of the bone to permit and encourage eruption of a new tooth.

FIGS. 7A, 7B, and 7C describes the placement of a cell composition in bone structure to achieve closure of spaces between teeth. Placement of the cell composition between teeth initiates bone regeneration, bone resorption and/or bone growth activation properties in the area between the teeth. This bone activity results in softening of the bone between the teeth and permits, through physical forces, the regrouping and closure of teeth around the gap.

For treatment of necrotic bone a scaffold like structure may be used to bioengineered the necrotic and/or healthy bone tissue. For example, an area of necrotic and/or healthy may be subject to bioengineering modification to place a scaffold like structure into and surrounding the necrotic bone tissue. Administration of the cells into and around the necrotic bone tissue may result in reactivation and/or regeneration of otherwise necrotic bone tissue.

In another aspect of the invention a necrotic bone condition is treated by maintaining the necrotic tissue and then used as a basis for forming a scaffold like structure which will be injected with the cells matrix to stimulate bone resorption, regeneration and formation.

When considering treatment for Osteonecrosis (ON) and/or Osteonecrosis of the Jaw (ONJ), administration of mononuclear cells and/or osteoclasts and/or hematopoietic stem cells may occur by the same route as given herein for the administration of osteoclasts for treatment of bone in need of remodeling. A computed tomography scan, or the like, can be used to provide a three-dimensional (3D) image of a targeted necrotic bone tissue. The treatment of ON and/or ONJ comprises accessing this site, and in one embodiment, an incision is made so as to form a flap of skin and/or muscle tissue(s) and concurrently expose the necrotic bone tissue. A scaffold like structure guide may be generated from the 3D image and indicates the placement, angulation, and depth of cylindrical cavities to be made on or into the targeted necrotic bone tissue. In one embodiment, the guide is placed on or adjacent to the exposed necrotic bone tissue. The guide directs the drilling of cylindrical cavities so as to form the scaffold like pattern disclosed herein. Drilling of the cylindrical cavities may occur using an electronic screw-tipped device as disclosed herein, or by other means known in the art. The scaffold-like structure, e.g., a bioengineered bone structure, is conformed so as to allow the greatest level of bone rebuilding and renewal. Bone in this area may re-form so as to not leave any voids, or cavities, in the bone tissue. The cylindrical cavities of this embodiment may also as to pass into the periosteum and/or compact bone, and/or healthy or necrotic bone in the case of both prevention of ON and ONJ, as well as treatment of ON and ONJ.

Figure 4B:
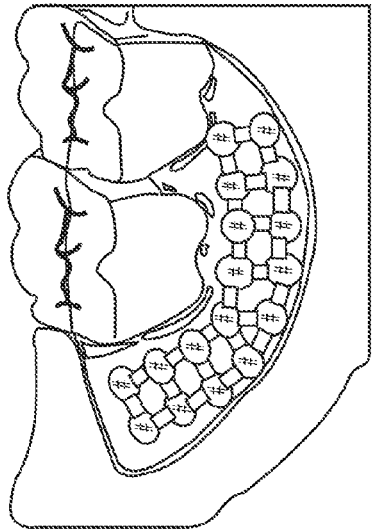
FIG. 4B shows the placement of the guide in the mouth.
Figure 4A:
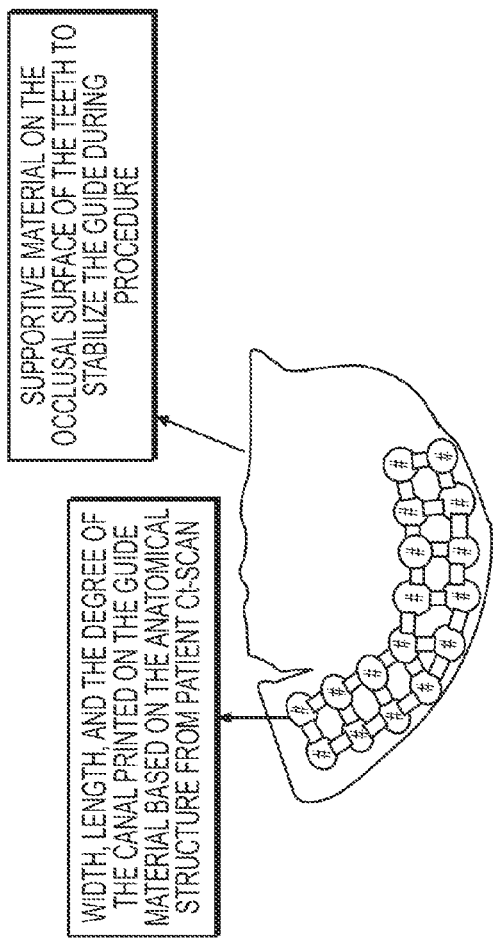
FIG. 4A shows a 3D CT scan generated customized guide for making scaffold like structure in a targeted bone tissue so as to bioengineer the bone.

FIG. 4 shows an embodiment of the present disclosure in which a CT scan is used to guide the formation of a scaffold-like bioengineered structure on bone. FIG. 4A shows a three-dimensional guide, preferably plastic, that is formed by utilizing a CT scan of a patient's bone structure in need of treatment. FIG. 4B shows placement of the guide in the mouth of a patient undergoing treatment and/or formation of a scaffold-like structure on one or more portions of an affected bone structure. The guide is placed to provide guidance and identification of portions of a bone structure or bone layer that are desirably imparted with a scaffold-like structure for later application of a cell-containing composition. FIG. 4C is a sagittal view describing the tissue structure and the bioengineered necrotic and/or healthy bone with the transplanted cells. FIG. 4D describes an embodiment of the invention in which the scaffold-like structure has a series of essentially perpendicular canals, i.e., perpendicular to the surface of the bone undergoing treatment, and a series of cavities angled obliquely relative to the perpendicular cavities. The angled cavities serve to connect the spaces within the perpendicularly oriented cavities. The angled cavities may connect 2, 3, 4, 5 or more perpendicular cavities such that the cavities are in fluid communication with one another.

After treatment, the necessary subsequent steps may be taken as in our previous embodiments. For example, perio dressing and/or periodontal dressing may be placed in the area of the engineered bone, once the osteoclast and/or HSC matrix has been released. When the cylindrical cavities involve the oral cavity, gauze is preferably employed so as to assure that the osteoclast and/or HSC matrix remains on site for an extended time. Further use of a chemical antiseptic and/or anesthetic at the site of the engineered bone is preferred; either prior to, during or immediately after the cylindrical cavities are formed in order to minimize the subject's risk of infection and discomfort.

As craniotomy is a highly invasive surgery, an established craniosynostosis model such as, but not limited to, a model as disclosed in U.S. Pat. No. 7,731,499 (incorporated herein by reference) can be utilized to assess the effects of the autologous cell composition of this disclosure on minimizing said surgical trauma. In addition to CT scans, various orthodontic models, such as a series of x-rays, or molds, can be used to show the rate of bone formation or tooth movement of subjects undergoing treatment by the method of this disclosure. Other methods for quantifying the level of bone remodeling activity include assessing the activity levels of cathepsin K, TRAP, and OPN protein levels. Such as assays are well known in the art and may be used alongside other measurements, such as the identification of the number of osteoclasts, and further identification of the number of TRAP-positive osteoclasts. In a preferred embodiment, the number of TRAP-positive osteoclasts may be increased by 100%-up to one-hundred-fold as compared to the number of TRAP-positive osteoclasts prior to any cylindrical cavities, and represents a further increase over the increased TRAP-positive osteoclast activity seen as a result of the bioengineered bone.

Figure 8A:
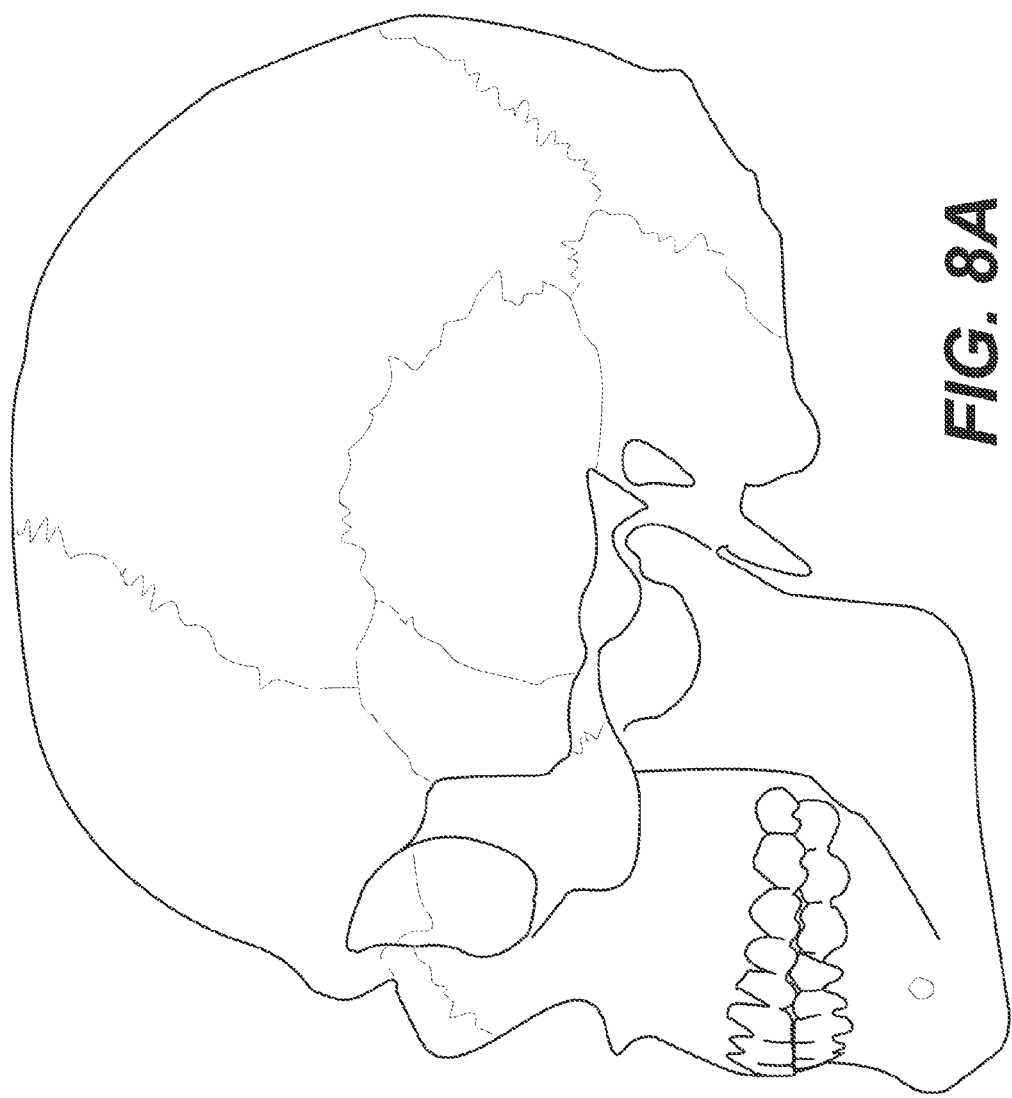
FIGS. 8A, 8B, 8C show the process of localized delivery of biocompatible compositions comprising a subject's autologous peripheral blood mononuclear cells and/or hematopoietic stem cells and/or cells, such as osteoclasts, obtained by the ex vivo differentiation of these cells for treatment of a synostotic condition.
Figure 8B:
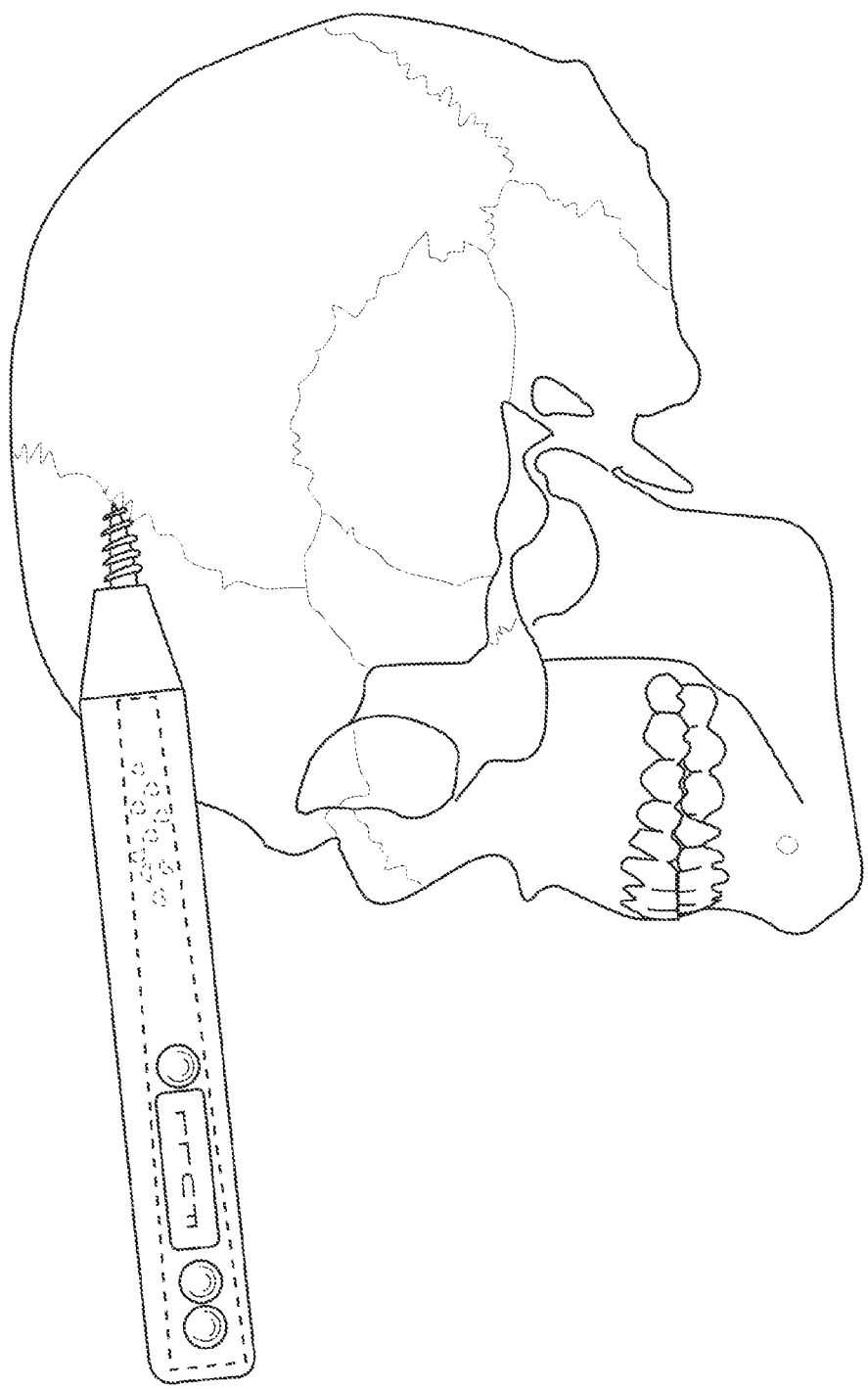
Figure 8C:
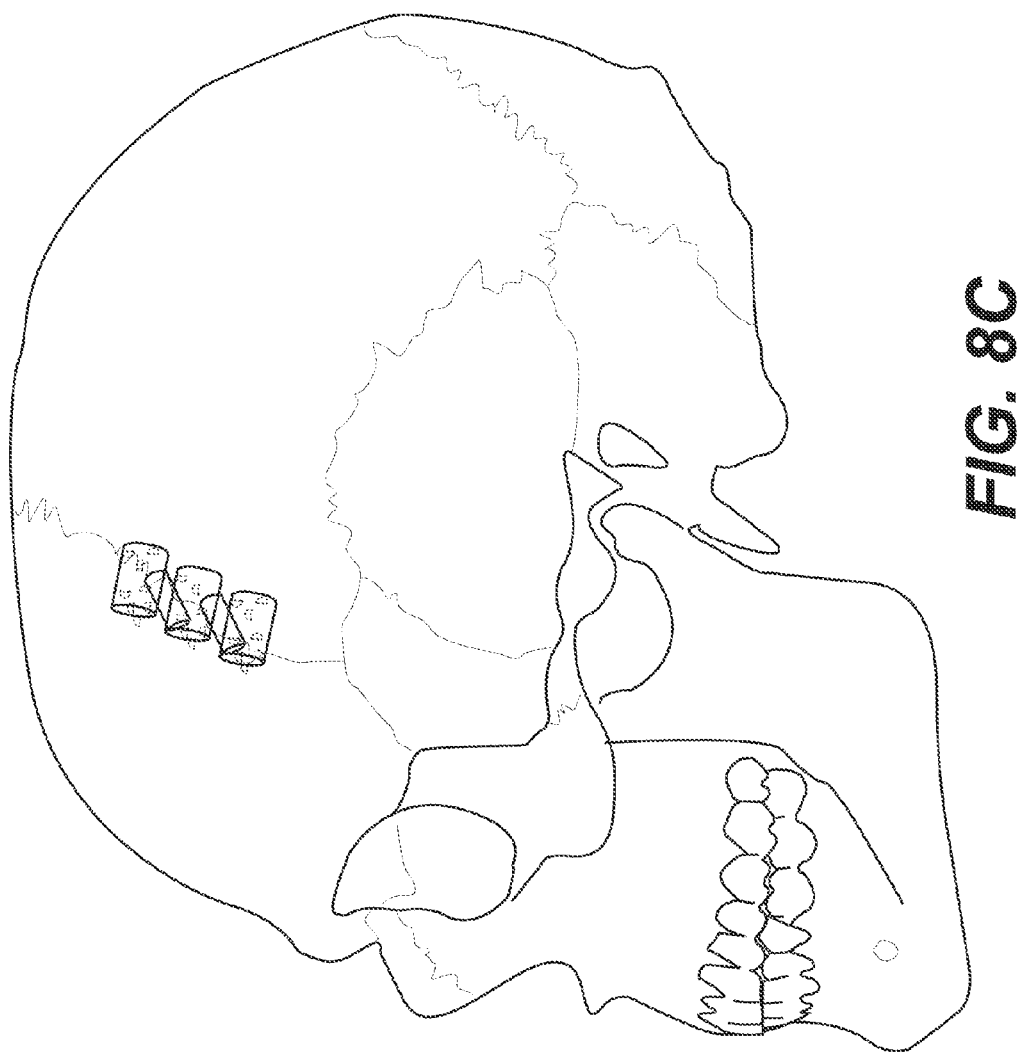

FIG. 8A shows the skull of a patient with sutures that define different parts of the cranium. FIG. 8B shows use of the device of the invention to create a scaffold-like structure in or around the sutures of a patient's cranium. FIG. 8C shows a scaffold-like structure to which has been applied a cell-containing composition. For example, osteoclasts may now be present in the cavities and/or pores of the scaffold-like structure located around a cranial suture.

Figure 9A:
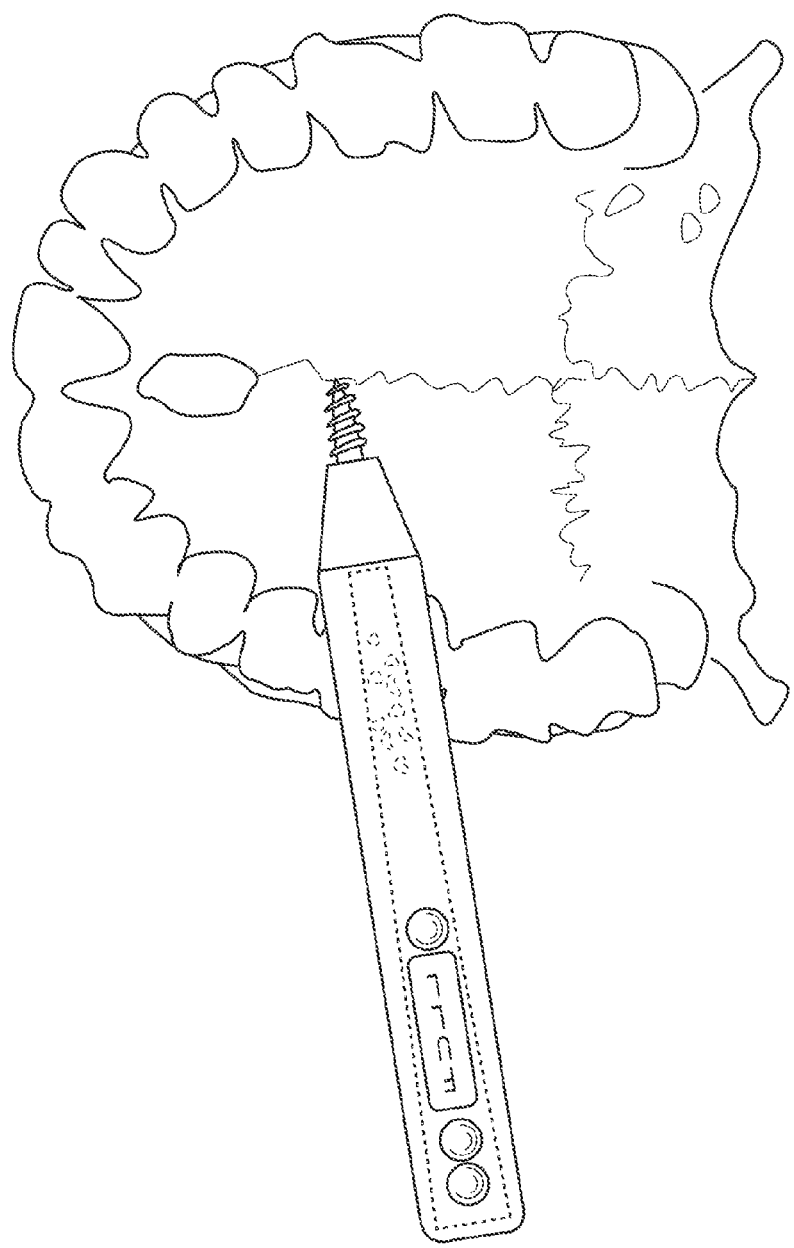
FIGS. 9A, 9B show the process of localized delivery of biocompatible compositions comprising a subject's autologous peripheral blood mononuclear cells and/or hematopoietic stem cells and/or monocytes and/or cells, such as osteoclasts, obtained by the ex vivo differentiation of these cells for treatment of a dentofacial condition.
Figure 9B:
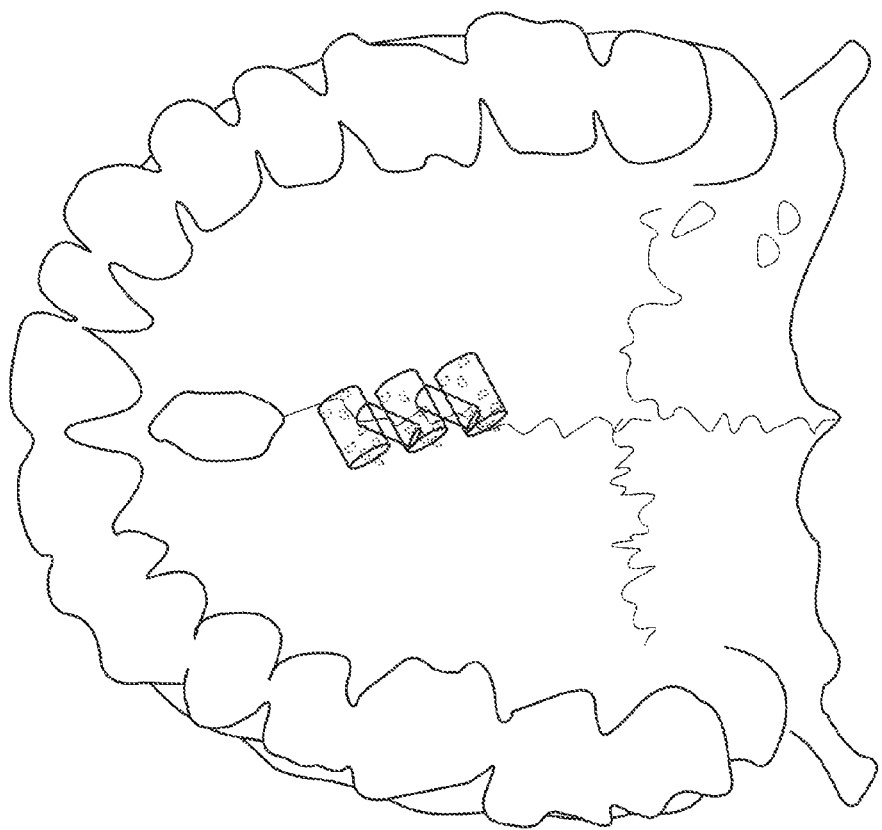

FIG. 9A shows an embodiment of the invention in which a cell-containing composition is delivered to a suture in an oral cavity. First, a scaffold-like structure is bioengineered to a suture area within the oral cavity. The scaffold-like structure is preferably bioengineered using a flap method whereby soft tissue surrounding the suture is first peeled back to reveal the underlying bone or without flap. Subsequently the device of the invention is utilized to form a series of perpendicular and angled cavities at an area of the suture requiring treatment. FIG. 9B shows placement of the cell-containing composition in a scaffold-like structure near, on or within a suture of an oral cavity.

The present method and device can be used in combination with orthodontic appliances when there is need for increased rate of tooth movement. This need may be due in part to severe skeletal discrepancies. The present method is performed in a relatively short period of time with minimal discomfort and minimal side effects to a subject undergoing treatment. The method allows for accelerated tooth movement in a shortened period of time with the movement being in any direction.

Herein the use of autologous cells obtained from a subject's peripheral blood is used to bioengineer a targeted dentofacial bone tissue. A blood sample is obtained from a subject undergoing the bioengineering of the targeted dentofacial bone tissue. Isolation of PBMCs and subsequent ex vivo inducement occurs in order to obtain active osteoclasts. The active osteoclasts at a concentration ranging from 1 cell to 2 million cells, preferably from about 10 cells to 1 million cells, most preferably from about 100 cells to 1,000 cells are then placed in a polysaccharide hydrogel matrix. Further additives to said matrix include an antibiotic from the cephalosporin class and a 0.9% saline solution to maintain isotonic conditions for said osteoclasts. A sterile cartridge is then filled to a pre-determined level with said prepared osteoclasts so as to deliver a biocompatible amount of said osteoclasts to said subject.

The process described herein can be repeated one to twenty times over the course of an orthopedic and/or orthodontic treatment to facilitate the mechanism of bone remodeling. The injections can be done under local anesthesia. During the remodeling process, subjects blood calcium levels can be monitored over several months to correct for any degree of hypercalcemia which may occur in those subjects in need of extensive bone resorption.

As indicated above, the application of heat or cold to the areas undergoing remodeling by the device and method of this disclosure will further influence the rate and degree of bone resorption. For example, heat will increase blood supply to the site thus encouraging the arrival of cytokines to the area for activation of said osteoclasts. The use of this technique will minimize the need of high orthodontic/orthopedic forces and maximize the biological response. The concentrations of PBMC-derived osteoclasts can be variable based on the desired length or degree of attenuation of suture ossification. Similarly the duration of sustained release can be modified by the manipulation of the compositions comprising the sustained release formulation such as for example modifying the percent of bio-stable polymers found with a sustained release polymer.

Figure 2:
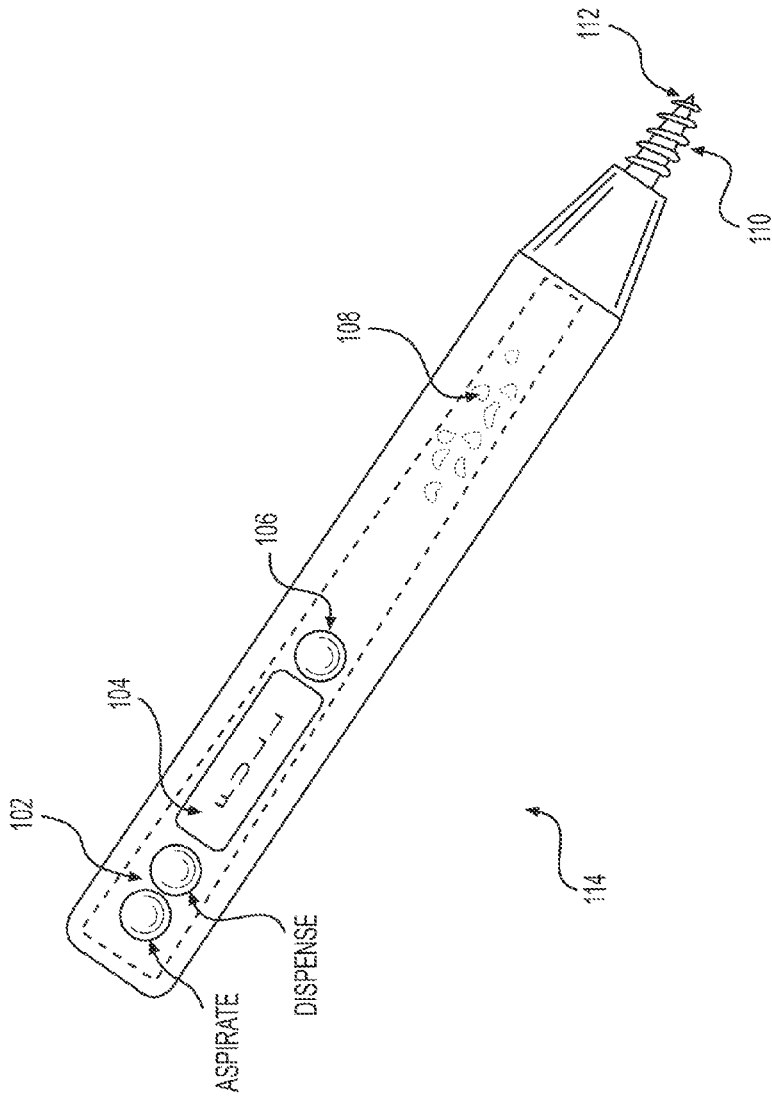
FIG. 2 shows the device for the localized administration of the cells of this disclosure.

FIG. 2 shows a device in the form of a hand-held instrument with an internal holder for storing as-prepared osteoclasts along with a screw tip designed to create cylindrical cavities in bone and soft tissue and release said osteoclasts and/or cells. The device includes a handle and a screw extending from the handle. The screw tip may be made of any compatible material used in surgical instrumentation, such as stainless steel. FIG. 2 illustrates the cell transplantation device 100 for injecting a prepared osteoclast and/or cells matrix 108 into tissue in need of bone remodeling or bone resorption. The device 100 allows for the drilling of a small cylindrical cavity for the insertion of the osteoclast and/or matrix 108. It has a control button 102 for the cell matrix injection and an informatics screen 104 both located at the distal end of the handle 114 for revealing parameters such as, but not limited to, temperature, speed of drilling, angulation, and depth of drilling. An adjacent control button 106 controls the motor (not shown) for the device 100. An internal cell holder tube provides a temperature insulated storage area for said osteoclast matrix 108. A screw tip 110 with one small hole in the tip 112 allows for the controlled release/injection of the osteoclast and/or matrix 108 either during the drilling process, or after the drilling process is complete. The screw tip 110 is rotatable with respect to the handle 114. In a preferred embodiment, the porous screw tip, bur, and/or needle have indicator markings, or stops, which indicate drilling depth and angulation.

In some embodiments the osteolysis device can further include a pressure transducer on the distal end of the handle to determine when the screw tip has fully penetrated the bone tissue or reached the pre-determined depth and angulation. An indicator mechanism, such as an indicator number on the screen of the device can be used to indicate that the screw tip has penetrated the bone to the desired extent depth and angulation. The screw tip 110 can have a length between 7 mm and 20 mm.

The device in FIG. 3A is designed to be used as a disposable device, or for re-use on the same subject. The device can optionally be configured to re-use the control/control indicator portions of the handle, while disposing of any parts of the device having direct contact with biological materials. The device is configured to deliver a fluid or gel matrix near or into the tissue during or upon completion of the drilling process. A cartridge 126 is located inside the handle and configured to hold the delivery fluid and autologous cells 108 held therein. A pump or actuator with a plunger 122 can be connected to the handle 114, which can cartridge 126 when pressure is applied thereto. Accordingly, fluid or gel from the cartridge 126 can travel through the fluid path in the handle 114 and a delivery channel 132 and out through the hole to be delivered to the subject at a localized area. The device 100 can be used to form cylindrical cavities in the jaw, or cranium or other targeted bone tissue.

The device 100 can be held at a range of 45 deg to 135 deg+/−10 degrees angle to a subject's bone. Pressure can be applied to the device, which, in combination with the rotation of the screw tip 110 can cause a cutting edge of the screw tip 110 to form one hole. Each hole can be formed in the bone near or at an excessive bone deposition site or malocclusion sought to be treated. The pressure and rotation can be stopped when the desired depth has been reached, such as when the screw tip has advanced to one of a predetermined marker on a guide placed on the targeted bone tissue.

FIG. 3B shows an embodiment of the invention in which the device includes a needle tip that is mounted directly on the delivery channel 132. The placement of a needle on the delivery channel permits injection of cells into a target area that may be smaller or more specifically defined than the target area that is formed by the screw 110.

Figure 3C:
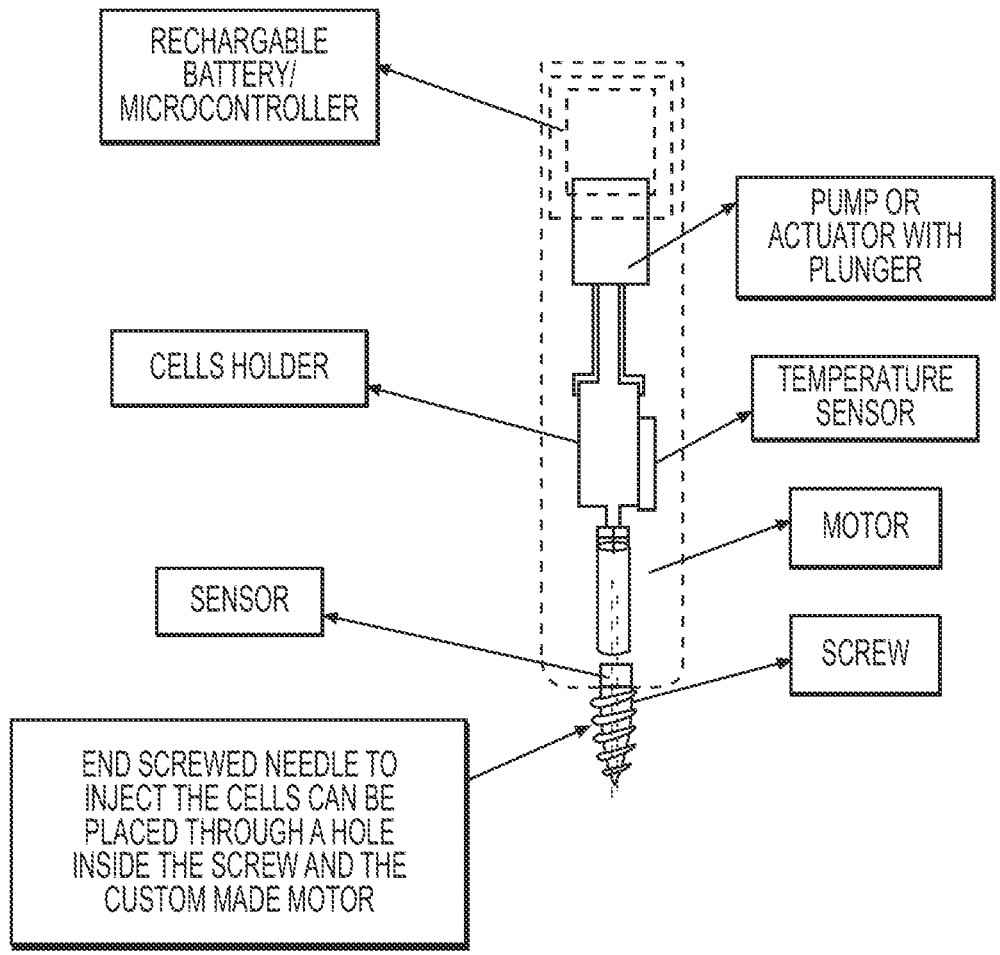
FIG. 3C shows an interior view of the device for the localized administration of the cells of this disclosure with a delivery needle held internal to the drilling screw tip.

FIG. 3C shows an embodiment of the device in which the axis of an injection needle is coaxial with the screw. In this embodiment of the invention of the needle may extend through the axis of the screw thereby permitting injection of a cell composition directly into a cavity formed by the screw without first removing the screw from the just type informed cavity.

The device can advantageously contain an adjustable-length screw tip 110 so as to allow the device to be controlled more precisely during the drilling process. It can accurately and safely be used in bone tissues of varying thickness and/or densities types.

As such, treatment can be tailored to provide the most beneficial level of autologous cell delivery.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for treating in situ a bone disease, bone disorder, or bone condition comprising:
    forming a series of substantially cylindrical cavities substantially perpendicular to a surface of a target bone of a subject that are interconnected via at least one substantially cylindrical cavity formed obliquely to the series of cylindrical cavities thus forming a scaffold-like structure in the bone;
    incorporating a composition comprising autologous osteoclasts into the scaffold-like structure.

2. The method of claim 1, wherein the target bone is a dentofacial bone.

3. The method of claim 1, wherein the target bone is a dentofacial bone forming a malocclusion.

4. The method of claim 1, wherein the bone disease, bone disorder, or bone condition is failure of tooth eruption.

5. The method of claim 1, wherein the subject is undergoing orthodontic treatment.

6. The method of claim 1 that further comprises:
    obtaining or deriving osteoclasts from peripheral blood of a subject having a malocclusion, having a failure of tooth eruption, or who is undergoing orthodontic treatment;
    forming a series of substantially cylindrical cavities substantially perpendicular to a surface of a dentofacial target bone of the subject; and
    incorporating said osteoclasts into the substantially cylindrical cavities.

7. The method of claim 1, wherein the target bone comprises a synostosis or fusion of two adjacent bones.

8. The method of claim 1, wherein the target bone comprises a synostosis or fusion of two adjacent skull bones.

9. The method of claim 1, wherein the target bone is at least one selected from the group consisting of a hallux abducto valgus deformity, osteocartilaginous exostosis, ankylosis, osteogenic sarcoma, an ectopic mineralization, a necrotic bone formed as a result of the progression of osteonecrosis, an osteoradionecrosis, and an osteonecrosis of the jaw.

10. The method of claim 1, wherein the scaffold-like structure comprises at least 20 to 1,000 partially intersecting substantially cylindrical cavities.

11. The method of claim 1, wherein the scaffold-like structure comprises substantially cylindrical cavities having a diameter ranging from 2.0 mm-5.0 mm.

12. The method of claim 1, wherein the scaffold-like structure comprises substantially cylindrical cavities having a depth ranging from 10 mm-50 mm.

13. The method of claim 1, wherein the scaffold-like structure comprises at least two perpendicular cavities at substantially a 90 degree angle to the surface of the bone and at least two oblique cavities that intersect the at least two perpendicular cavities at substantially a 90 degree angle.

14. The method of claim 1, wherein the scaffold-like structure comprises at least two perpendicular cavities at substantially a 90 degree angle to the surface of the bone and at least two oblique cavities at an oblique angle between 45 and 135 degrees to the surface of the bone.

15. The method of claim 1, wherein the osteoclast is derived from a peripheral blood mononuclear cell (PBMC).

16. The method of claim 1, wherein the osteoclast is derived from a hematopoietic stem cell (HSC).

17. The method of claim 1 that comprises incorporating a composition comprising 1 to 2 million PBMC-derived osteoclasts and/or HSC-derived osteoclasts into the scaffold-like structure.

18. The method of claim 1 that further comprises incorporating a hematopoietic stem cell into the scaffold-like structure.

19. The method of claim 1, wherein the autologous osteoclasts are incorporated along with at least one pH buffer, growth factor, antibiotic, or silver nanoparticle.

20. The method of claim 1, wherein the autologous osteoclasts have been incorporated into a pharmaceutically acceptable carrier delivery system comprising at least one of a polysaccharide hydrogel matrix, polyethylene glycol, polylactide, polyglycolide, collagen, alginate, or agarose.

21. The method of claim 1, further comprising:
    obtaining a 3D image of the target bone tissue,
    generating a scaffold-like structure guide from the 3D image,
    placing the scaffold-like structure guide on or adjacent to the target bone tissue, and
    following the guide to drill the substantially cylindrical cavities in the target bone.

22. The method of claim 1, wherein the autologous osteoclasts are incorporated into the scaffold-like structure by an electronic osteolysis device comprising:
    a first tip configured to penetrate bone;
    a second porous, hollow tip configured so as to be interchanged with the first tip configured to penetrate bone; and
    a handle comprising a distal end and a proximal end;
    wherein the proximal end comprises a control panel and internal controls, the distal end comprises a cartridge containing autologous osteoclasts and a plunger configured to draw the autologous cells into the cartridge and/or to cause the autologous osteoclasts to leave the cartridge and travel through the second porous, hollow tip.

* * * * *